US012697290B2

(12) United States Patent
Arhamah

(10) Patent No.: US 12,697,290 B2
(45) Date of Patent: Aug. 4, 2026

(54) COSMETIC COMPOUNDS HAVING TWO LINKED MALEIMIDE GROUPS, COSMETIC PREPARATIONS, AND METHOD FOR TREATMENT OF KERATIN MATERIALS

(71) Applicant: TARA BRANDS EUROPE S.L.U., Badalona (ES)

(72) Inventor: Nawaf Arhamah, Badalona (ES)

(73) Assignee: TARA BRANDS EUROPE S.L.U., Badalona (ES)

( * ) Notice: Subject to any disclaimer, the term of this patent is extended or adjusted under 35 U.S.C. 154(b) by 306 days.

(21) Appl. No.: 18/271,623

(22) PCT Filed: Jan. 17, 2023

(86) PCT No.: PCT/EP2023/050990

§ 371 (c)(1),
(2) Date: Jul. 10, 2023

(87) PCT Pub. No.: WO2023/135329

PCT Pub. Date: Jul. 20, 2023

(65) Prior Publication Data

US 2025/0017836 A1 Jan. 16, 2025

(30) Foreign Application Priority Data

Jan. 17, 2022 (EP) .................................... 22382019

(51) Int. Cl.
*A61K 8/49* (2006.01)
*A61Q 5/00* (2006.01)
*C07D 207/452* (2006.01)

(52) U.S. Cl.
CPC .............. *A61K 8/4913* (2013.01); *A61Q 5/00* (2013.01); *C07D 207/452* (2013.01)

(58) Field of Classification Search
CPC .................................................. C07D 207/452
See application file for complete search history.

(56) References Cited

U.S. PATENT DOCUMENTS

| | | | | |
|---|---|---|---|---|
| 7,160,946 B2 * | 1/2007 | Takano | C08F 8/34 528/170 |
| 2005/0245635 A1 * | 11/2005 | Takeda | C09J 4/00 522/90 |
| 2008/0075965 A1 | 3/2008 | Dershem | |
| 2012/0049106 A1 | 3/2012 | Dershem | |
| 2015/0337147 A1 | 11/2015 | Mayo et al. | |

FOREIGN PATENT DOCUMENTS

| | | |
|---|---|---|
| JP | 2011-219539 A | 11/2011 |
| WO | WO 2009/145779 A1 | 12/2009 |
| WO | WO 2018/060724 A1 | 4/2018 |
| WO | WO 2021/113415 A1 | 6/2021 |
| WO | WO 2022/183481 * | 9/2022 |

OTHER PUBLICATIONS

EPO (Rijswijk, NL), English language version of the International Search Report, Form PCT/ISA/210, for International Application PCT/EP2023/050990, Feb. 8, 2023 (4 pp.).
EPO (Munich, DE), English language Written Opinion of the International Searching Authority, Form PCT/ISA/237, for Int'l Appln. PCT/EP2023/050990, Feb. 8, 2023 (8 pp.).
JPPO, "Notice of Reasons for Refusal" for Japanese Patent Application No. JP 2024-542252, Issued Feb. 17, 2026 (5 pages).
Neville D. et al., "Enhancement of Immunotoxin Efficacy by Acid-cleavable Cross-linking Agents Utilizing Diphtheria Toxin & Toxin Mutants," Sep. 6, 1989, vol. 264, No. 26 p. 14653-14661, The Journal of Biological Chemistry.

* cited by examiner

*Primary Examiner* — Valerie Rodriguez-Garcia
(74) *Attorney, Agent, or Firm* — Pauley Erickson & Swanson

(57) ABSTRACT

Disclosed herein is a compound or pharmaceutically acceptable salt thereof of formula I:

I

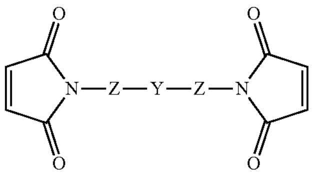

wherein Y is a C3-11 cycloalkyl and Z is straight-chain or branched C1-14 alkyl, wherein one or more CH2 groups may independently be replaced by —(CH2—O—CH2)—, —(CH2—CH2—O)—, —(O—CH2—CH2)—, C═O, —O—, —NH— and —NR—, wherein R is linear or branched C1-6 alkyl. Further disclosed are cosmetic preparations including compounds of formula I as well as uses of such compounds or preparations as hair care products.

14 Claims, No Drawings

COSMETIC COMPOUNDS HAVING TWO LINKED MALEIMIDE GROUPS, COSMETIC PREPARATIONS, AND METHOD FOR TREATMENT OF KERATIN MATERIALS

CROSS REFERENCE TO RELATED APPLICATION

This application is a National Phase filing in the United States, under 35 USC § 371, of PCT International Patent Application Number PCT/EP2023/050990, filed on 17 Jan. 2023 which claims the priority of European Patent Application Number EP 22382019.2, filed 17 Jan. 2022.

The above-referenced PCT Application is hereby incorporated by reference herein in its entirety and is made a part hereof, including but not limited to those portions which specifically appear hereinafter.

BACKGROUND OF THE INVENTION

Field of the Invention

The present disclosure relates to compounds and cosmetic preparations and their use as hair care products. Further disclosed is a method for treatment of keratin materials, such as hair.

Discussion of Related Art

Human hair has a highly organized but complex structure. It is composed of the hair follicle, which is embedded in the skin, and hair shaft, which extends out of the skin. Hair is typically composed of two or three layers. The outermost layer is the cuticle, the middle layer is the cortex and in some cases there is a central medulla region that is made of packed cells and/or hollow spaces. A large part of the mass of the human hair is composed of fibrous structures called macrofibrils, each one consists of microfibrils held together by matrix proteins. Human hair consists of 65-95 wt % proteins, predominantly keratin which is a fibrous, helicoidal protein particularly rich in the amino acid cysteine, whose thiol groups may form disulfide crosslinks adding rigidity and resistance to the entire hair structure.

There are various treatments for hair, such as bleaching, dyeing, straightening and permanent waving, during which hair may become overprocessed or damaged due to the chemicals needed to effect the change desired. For example, some known hair straightening processes consist of treatment with alkaline straightener. The high pH (9.0-14.0) causes the hair to swell, which allows the alkaline agent to penetrate into the hair fibers, where it reacts with keratin and causes breaking and rearranging of the disulfide bridges present in keratin, allowing hair to be stretched. In addition to chemically caused damage, physical treatments such as frequent and/or high heat or environmental exposure may produce changes in hair texture and lead to further often permanent damage.

SUMMARY OF THE INVENTION

It would be highly desirable to be able to avoid, minimize, alleviate or repair any such damage that occurs during those hair treatment processes and in particular to restore disulfide bridges to regain and improve hair quality, strength and texture.

It is an object of the present disclosure to advance the state of the art of hair repair. It is a further object of the present disclosure to provide compounds and preparations for use as hair care products, which are preferably able to crosslink thiol moieties. The thiol moieties to be crosslinked may, for example, have been formed by cleavage of disulfide bridges as a result of physical or chemical hair treatments. It is a further object of the present disclosure to enhance the restoration of disulfide bridges using the inventive linkers in hair.

Applicants have developed thiol-reactive crosslinking agents which are capable of cross-linking thiol moieties, thus emulating disulfide bridges. The thiol moieties to be cross-linked may, for example, result from prior cleavage of disulfide bridges, e.g. as a result of physical or chemical hair treatments. By crosslinking the thiol moieties, the thiol-reactive crosslinking agents disclosed herein effective enable restoration of disulfide bridges.

The thiol-reactive crosslinking agents disclosed herein comprise at least two electrophiles which are linked by a fragment comprising at least one C3-11 cycloalkyl group. The electrophiles may be selected from maleimide, dithiopyridyl, α-halo carbonyl, among others. The C3-11 cycloalkyl may, for example, be C3-11 bicycloalkyl, such as C3-11 bridged bicycloalkyl. It was found that, surprisingly, including at least one C3-11 cycloalkyl group as part of the fragment linking the electrophiles enhances the volume and the slickness of the hair treated with the thiol-reactive cross-linking agents. Furthermore, the at least one C3-11 cycloalkyl group possess a well-defined hydrophobicity which, being part of the fragment linking the electrophiles, renders the thiol-reactive crosslinking agents amphiphilic. Additionally, C3-11 cycloalkyl groups are non-invasive and environmentally benign, which contributes to enhanced safety and reduced toxicology.

The present disclosure is in a first aspect directed to compounds of formula I or a pharmaceutically acceptable salt thereof wherein Y is a C3-11 cycloalkyl, Z is straight-chain or branched C1-14 alkyl, wherein one or more CH2 groups may independently be replaced by —(CH2—O—CH2)—, —(CH2—CH2—O)—, —(O—CH2—CH2)—, C═O, —O—, —NH— and —NR—, wherein R is linear or branched C1-6 alkyl.

In some embodiments, the present disclosure is directed towards a compound of formula II or a pharmaceutically acceptable salt thereof wherein Y is a C3-11 cycloalkyl, L is selected from CH2 and C═O, Z is straight-chain or branched C1-13 alkyl, wherein one or more CH2 groups may independently be replaced by —(CH2—O—CH2)—, —(CH2—CH2—O)—, —(O—CH2—CH2)—, —O—, —NH—, and —NR—, wherein R is linear or branched C1-6 alkyl.

In some embodiments of a compound of formula I or II or a pharmaceutically acceptable salt thereof, Y is a C3-11 bicycloalkyl, such as a C4-11 bridged bicycloalkyl.

In some embodiments, the present disclosure is directed towards a compound of formula III or a pharmaceutically acceptable salt Y is a C4-11 bicycloalkyl, X is selected from O, NH and NR, wherein R is linear or branched C1-6 alkyl, Z is straight-chain or branched C1-12 alkyl, wherein one or more CH2 groups may independently be replaced by —(CH2—O—CH2)—, —(CH2—CH2—O)—, —(O—CH2—CH2)—, —O—, —NH—, and —NR—, wherein R is branched or linear C1-6 alkyl.

In some embodiments, the present disclosure is directed towards a compound of formula IV or a pharmaceutically acceptable salt thereof wherein Y is a C5-11 bridged bicycloalkyl, Z is straight-chain or branched C1-11 alkyl, wherein one or more CH2 groups may independently be replaced by —(CH2—O—CH2)—, —(CH2—CH2—O)—, —(O—CH2—CH2)—, —O—, —NH—, and —NR—, wherein R is branched or linear C1-6 alkyl.

In some embodiments, the present disclosure is directed towards a compound of formula V or a pharmaceutically acceptable salt thereof wherein Y is a C5-11 bridged bicycloalkyl, G is —(CH2—O—CH2)—, —(CH2—CH2—O)—, —(O—CH2—CH2)—, n is 1 to 4, preferably 2 or 3, and m is 0 to 8, preferably 0 to 3.

In some embodiments of a compound of formula V n is 2 or 3. In some embodiments of a compound of formula V m is 0, 1, 2, or 3.

In some embodiments of a compound of formula V, Y is bicyclo[1.1.1]pentane, n is 2 or 3, and m is 0, 1, 2 or 3;

In some embodiments of a compound of formula V, Y is bicyclo[2.2.2]octane, n is 3, and m is 0.

In some embodiments of a compound of any one of formulae I-V, Y is selected from bicyclo[1.1.1]pentane, bicyclo[2.1.1]hexane, bicyclo[2.2.1]heptane, bicyclo[3.1.1]heptane, bicyclo[2.2.2]octane, bicyclo[3.2.1]octane, preferably bicyclo[1.1.1]pentane and bicyclo[2.2.2]octane.

In a second aspect, the disclosure is directed to a cosmetic preparation comprising at least one compound according to any of the embodiments described herein.

In some embodiments of the cosmetic preparation, the cosmetic preparation further comprises at least one cosmetic additive selected from the group consisting of surfactants, oil components, emulsifiers, pearlescent waxes, consistency-enhancing agents, thickeners, superfatting agents, stabilizers, polymers, silicone compounds, fats, waxes, lecithins, phospholipids, UV light protection factors, humectants, biogenic agents, antioxidants, deodorants, antiperspirants, antidandruff agents, film-forming agents, swelling agents, insect repellents, self-tanning agents, tyrosine inhibitors (depigmentation agents), hydrotropes, solubilizers, preservatives, perfumed oils and dyes, as well as mixtures thereof.

In some embodiments of the cosmetic preparation, the cosmetic preparation further comprises a carrier, preferably a carrier selected from water, C(2-6)-alcohols, C(1-10) polyols, as well as oil components.

In a third aspect, the disclosure is directed to a composition or a cosmetic preparation according to any of the embodiments described herein, for use as hair care products.

In a fourth aspect, the disclosure is directed to the use of compounds according to any of the embodiments described herein, for the production of cosmetic preparations, preferably hair care products.

In a fifth aspect, the disclosure is directed to a method for treatment of keratin materials, such as hair, the method comprising applying to the keratin materials a compound or a cosmetic preparation according any of the embodiments described herein. The method relates in particular to the cosmetic treatment of keratin materials, such as hair.

The compounds and cosmetic preparations disclosed herein are suitable for cosmetic use, in particular for the protection of healthy hair or the amelioration of damaged hair.

DETAILED DESCRIPTION OF THE INVENTION

In the context of the present disclosure, restoration of disulfide bridges refers to a process by which two thiol moieties are linked together (it is understood that the term “disulfde bridges” refers to two thiol moieties being linked using the compounds of the invention and not directly linked —S—S-bonds). The thiol moieties may, for example, be part of keratin protein. The process of linking the thiol moieties together may involve reaction of each thiol with an electrophilic moiety in the crosslinking agent. The thiol-reactive crosslinking agents disclosed herein typically react with two thiol moieties to form a crosslinking unit which links the two thiol moieties together.

Unless specified otherwise the following general definitions apply to all compounds of the disclosure according to the description.

The term “compound of the disclosure” as used herein, refers to compounds represented by formulae I-V (including salts and stereosiomers thereof) and any of the specific examples disclosed herein.

It is understood that “independently of each other” means that when a group is occurring more than one time in any compound, its definition on each occurrence is independent from any other occurrence.

It is further understood that a dashed line or a wave being transverse to a bond or a solid line without attachment, such as —$C_{1-4}$ alkyl, depicts the site of attachment of a residue (i.e. a partial formula).

It is further understood that the abbreviations “C” and “N” are representative for all possible degrees of saturation, which typically do not result in radicals, nitrenes or carbenes, i.e. N includes —NH—, —N= and

,

C includes —$CH_2$—, =CH— and

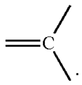.

In addition, “C” as an atom in an aromatic or heteroaromatic ring which has a substituent $R^x$ at any suitable position, includes =CH— as well as =$CR^x$—. In addition, “C” as an atom in an aromatic or heteroaromatic ring which does not have substituents $R^x$ at any suitable position, includes =CH— and

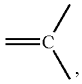, as the case may be. It is understood and known to the skilled person that the general rules of valency must be abided by.

The term "saturated" in reference to ring systems refers to a ring having no double or triple bonds. The term "partially unsaturated" in reference to ring systems refers to a ring that includes at least one double or triple bond but does not include aromatic systems.

It is understood that whenever, in any formula, more than one $CH_2$ group of a straight-chain or branched alkyl chain, e.g. straight-chain or branched $C_{2-25}$ alkyl, is replaced by a heteroatom or a heteroatom-containing groups, the two or more $CH_2$ groups are replaced such that directly adjacent heteroatoms, e.g. —O—O— or —NH—NH—, are avoided. In particular, the two or more $CH_2$ groups shall be replaced such that the alkyl chain does not contain peroxide groups. The same holds true for the selection of generic groups defined herein, such as G or Z, which are selected such that directly adjacent heteroatoms, e.g. —O—O— or —NH—NH—, are avoided.

The term "$C_{3-11}$ cycloalkyl" refers to saturated or partially unsaturated alkyl ring systems containing 3, 4, 5, 6, 7, 8, 9, 10 or 11 carbon atoms and comprises monocycles, fused bicycles, bridged bicycles or spirobicycles. In some embodiments, the term "$C_{3-11}$ cycloalkyl" refers to saturated alkyl ring systems containing 3, 4, 5, 6, 7, 8, 9, 10 or 11 carbon atoms and comprises monocycles, fused bicycles, bridged bicycles or spirobicycles.

Examples of "$C_{3-11}$ cycloalkyl" include monocycles, such as cyclopropyl, cyclobutyl, cyclopentyl, cyclohexyl; bridged bicycles, such as bicyclo[1.1.1]pentane, bicyclo[2.1.1]hexane, bicyclo[2.2.1]heptane, bicyclo[2.2.2]octane, bicyclo[3.2.1]octane, bicyclo[3.2.2]nonane, bicyclo[3.3.1]nonane; fused bicycles, such as bicyclo[2.1.0]pentane, bicyclo[2.2.0]hexane, bicyclo[3.1.0]hexane, bicyclo[3.2.0]heptane, bicyclo[4.1.0]heptane, bicyclo[4.2.0]octane, bicyclo[4.3.0]nonane, bicyclo[4.4.0]decane, spirocycles, such as spiro[2.2]pentane, spiro[2.3]hexane, spiro[3.3]heptane, spiro[3.4]octane, spiro[4.4]nonane, spiro[3.5]nonane, spiro[4.5]decane, spiro[5.5]undecane.

In some embodiments, $C_{3-11}$ cycloalkyl is $C_{4-11}$ bicycloalkyl. In some embodiments, $C_{3-11}$ cycloalkyl is $C_{5-11}$ bridged bicycloalkyl. In some embodiments, $C_{3-11}$ cycloalkyl is $C_{4-11}$ fused bicycloalkyl. In some embodiments, $C_{3-11}$ cycloalkyl is $C_{5-11}$ spirocycloalkyl. In some embodiments, $C_{3-11}$ cycloalkyl is selected from bicyclo[1.1.1]pentane, bicyclo[2.1.1]hexane, bicyclo[2.2.1]heptane, bicyclo[3.1.1]heptane, bicyclo[2.2.2]octane, bicyclo[3.2.1]octane, preferably bicyclo[1.1.1]pentane and bicyclo[2.2.2]octane.

A "$C_{3-11}$ cycloalkyl" group has two points of attachment. A point of attachment is an atom which forms a covalent bond with another atom to which the group is attached. The two points of attachment may be located at the same or different atoms.

The terms "$C_{1-14}$ alkyl", "$C_{1-12}$ alkyl", "$C_{1-11}$ alkyl" and "$C_{1-6}$ alkyl" refer to a fully saturated branched or unbranched hydrocarbon moiety having the indicated number of carbon atoms. Representative examples of $C_{1-14}$ alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, iso-hexyl, neohexyl, heptyl, octyl, nonyl, decyl, dodecyl, etc. Representative examples of $C_{1-6}$ alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, iso-hexyl or neohexyl. One or more adjacent or non-adjacent $CH_2$ groups of $C_{1-14}$ alkyl, $C_{1-12}$ alkyl, $C_{1-11}$ alkyl and $C_{1-6}$ alkyl may independently be replaced by one or more groups selected from —($CH_2$—O—$CH_2$)—, —($CH_2$—$CH_2$—O)—, and —(O—$CH_2$—$CH_2$)—, —O—, —NH—, —NR—, wherein R is linear or branched $C_{1-6}$ alkyl.

Based on the definitions given throughout the application the skilled person knows which combinations are synthetically feasible and realistic, e.g. typically combinations of groups leading to some heteroatoms directly linked to each other, e.g. —O—O—, are not contemplated, however synthetically feasible combinations, such as —S—N= in aisothiazole are contemplated.

In a first aspect, the disclosure is directed towards a compound of formula I

I

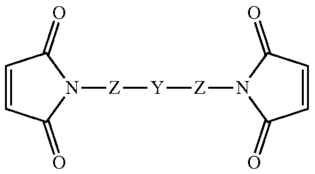

wherein

Y is $C_{3-11}$ cycloalkyl,

Z is straight-chain or branched $C_{1-14}$ alkyl, wherein one or more $CH_2$ groups may independently be replaced by —($CH_2$—O—$CH_2$)—, —($CH_2$—$CH_2$—O)—, and —(O—$CH_2$—$CH_2$)—, C═O, —O—, —NH— and —NR—, wherein R is linear or branched $C_{1-6}$ alkyl.

In some embodiments of a compound of formula I, Y is $C_{4-11}$ bicycloalkyl. In some embodiments of a compound of formula I, Y is $C_{5-11}$ bridged bicycloalkyl. In some embodiments of a compound of formula I, Y is $C_{4-11}$ fused bicycloalkyl. In some embodiments of a compound of formula I, Y is $C_{5-11}$ spirocycloalkyl.

In some embodiments of a compound of formula I, Y is selected from bicyclo[1.1.1]pentane, bicyclo[2.1.1]hexane, bicyclo[2.2.1]heptane, bicyclo[3.1.1]heptane, bicyclo[2.2.2]octane, bicyclo[3.2.1]octane, preferably bicyclo[1.1.1]pentane and bicyclo[2.2.2]octane.

In some embodiments of a compound of formula II, Z is straight-chain or branched $C_{1-14}$ alkyl. In some embodiments of a compound of formula II, Z is straight-chain or branched $C_{1-14}$ alkyl, wherein one or more $CH_2$ groups is independently replaced by —($CH_2$—O—$CH_2$)—, —($CH_2$—$CH_2$—O)—, —(O—$CH_2$—$CH_2$)—, —O—, —NH—, and —NR—, wherein R is linear or branched $C_{1-6}$ alkyl.

In some embodiments of a compound of formula I, Z is straight-chain or branched $C_{1-14}$ alkyl, wherein one or more $CH_2$ groups may independently be replaced by —($CH_2$—O—$CH_2$)—, —($CH_2$—$CH_2$—O)—, —(O—$CH_2$—$CH_2$)—, C═O, and —O—.

In some embodiments of a compound of formula I, Z is straight-chain or branched $C_{1-10}$ alkyl, wherein one or more $CH_2$ groups may independently be replaced by —($CH_2$—O—$CH_2$)—, —($CH_2$—$CH_2$—O)—, —(O—$CH_2$—$CH_2$)— and —O—.

In some embodiments of a compound of formula I, Z is straight-chain or branched $C_{1-8}$ alkyl, wherein up to five $CH_2$ groups may independently be replaced by —($CH_2$—O—$CH_2$)—, —($CH_2$—$CH_2$—O)—, —(O—$CH_2$—$CH_2$)—, and —O—.

In some embodiments, the compound of the invention is of formula II

II

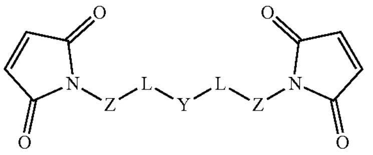

wherein

Y is a $C_{3-11}$ cycloalkyl,

L is selected from $CH_2$ and C═O,

Z is straight-chain or branched $C_{3-11}$ alkyl, wherein one or more $CH_2$ groups may independently be replaced by —($CH_2$—O—$CH_2$)—, —($CH_2$—$CH_2$—O)—, —(O—$CH_2$—$CH_2$)—, —O—, —NH—, and —NR—, wherein R is linear or branched $C_{1-6}$ alkyl.

In some embodiments of a compound of formula II, Z is straight-chain or branched $C_{1-13}$ alkyl. In some embodiments of a compound of formula II, Z is straight-chain or branched $C_{1-13}$ alkyl, wherein one or more $CH_2$ groups is independently replaced by —($CH_2$—O—$CH_2$)—, —($CH_2$—$CH_2$—O)—, —(O—$CH_2$—$CH_2$)—, —O—, —NH—, and —NR—, wherein R is linear or branched $C_{1-6}$ alkyl.

In some embodiments of a compound of formula II, L is $CH_2$. In some embodiments of a compound of formula II, L is C═O.

In some embodiments of a compound of formula II, Y is $C_{4-11}$ bicycloalkyl. In some embodiments of a compound of formula II, Y is $C_{5-11}$ bridged bicycloalkyl. In some embodiments of a compound of formula II, Y is $C_{4-11}$ fused bicycloalkyl. In some embodiments of a compound of formula II, Y is $C_{5-11}$ spirocycloalkyl.

In some embodiments of a compound of formula II, Y is selected from bicyclo[1.1.1]pentane, bicyclo[2.1.1]hexane, bicyclo[2.2.1]heptane, bicyclo[3.1.1]heptane, bicyclo[2.2.2]octane, bicyclo[3.2.1]octane, preferably bicyclo[1.1.1]pentane and bicyclo[2.2.2]octane.

In some embodiments of a compound of formula II, L is $CH_2$ and Y is $C_{4-11}$ bicycloalkyl, preferably $C_{5-11}$ bridged bicycloalkyl. In some embodiments of a compound of formula II, L is C═O and Y is $C_{4-11}$ bicycloalkyl, preferably $C_{5-11}$ bridged bicycloalkyl.

In some embodiments of a compound of formula II, L is $CH_2$ and Y is selected from bicyclo[1.1.1]pentane, bicyclo[2.1.1]hexane, bicyclo[2.2.1]heptane, bicyclo[3.1.1]heptane, bicyclo[2.2.2]octane, bicyclo[3.2.1]octane, preferably bicyclo[1.1.1]pentane and bicyclo[2.2.2]octane. In some embodiments of a compound of formula II, L is C═O and Y is selected from bicyclo[1.1.1]pentane, bicyclo[2.1.1]hexane, bicyclo[2.2.1]heptane, bicyclo[3.1.1]heptane, bicyclo[2.2.2]octane, bicyclo[3.2.1]octane, preferably bicyclo[1.1.1]pentane and bicyclo[2.2.2]octane.

In some embodiments of a compound of formula II, Z is straight-chain or branched $C_{1-13}$ alkyl, wherein one or more $CH_2$ groups may independently be replaced by —($CH_2$—O—$CH_2$)—, —($CH_2$—$CH_2$—O)—, —(O—$CH_2$—$CH_2$)—, and —O—.

In some embodiments of a compound of formula II, Z is straight-chain or branched $C_{1-10}$ alkyl, wherein one or more $CH_2$ groups may independently be replaced by —($CH_2$—O—$CH_2$)—, —($C_2$—$CH_2$—O)—, —(O—$CH_2$—$CH_2$)— and —O—.

In some embodiments of a compound of formula II, Z is straight-chain or branched $C_{1-8}$ alkyl, wherein up to five $CH_2$ groups may independently be replaced by —($CH_2$—O—$CH_2$)—, —($CH_2$—$CH_2$—O)—, —(O—$CH_2$—$CH_2$)—, and —O—.

In some embodiments, the compound of the invention is of formula III

III

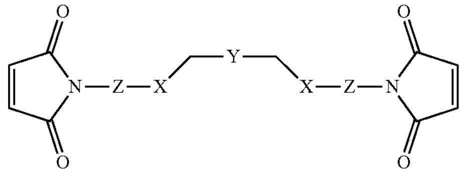

wherein

Y is a $C_{4-11}$ bicycloalkyl,

X is selected from O, NH and NR, wherein R is linear or branched $C_{1-6}$ alkyl, Z is straight-chain or branched $C_{1-12}$ alkyl, wherein one or more $CH_2$ groups may independently be replaced by —($CH_2$—O—$CH_2$)—, —($CH_2$—$CH_2$—O)—, —(O—$CH_2$—$CH_2$)—, —O—, —NH—, and —NR—, wherein R is branched or linear $C_{1-6}$ alkyl.

In some embodiments of a compound of formula III, Z is straight-chain or branched $C_{1-12}$ alkyl. In some embodiments of a compound of formula III, Z is straight-chain or branched $C_{1-12}$ alkyl, wherein one or more $CH_2$ groups are independently replaced by —($CH_2$—O—$CH_2$)—, —($CH_2$—$CH_2$—O)—, —(O—$CH_2$—$CH_2$)—, —O—, —NH—, and —NR—, wherein R is branched or linear $C_{1-6}$ alkyl.

In some embodiments of a compound of formula III, X is O. In some embodiments of a compound of formula III, X is NH. In some embodiments of a compound of formula III, X is NR, wherein R is branched or linear $C_{1-6}$ alkyl.

In some embodiments of a compound of formula III, Y is $C_{5-11}$ bridged bicycloalkyl. In some embodiments of a compound of formula III, Y is $C_{4-11}$ fused bicycloalkyl. In some embodiments of a compound of formula III, Y is $C_{5-11}$ spirocycloalkyl.

In some embodiments of a compound of formula III, Y is selected from bicyclo[1.1.1]pentane, bicyclo[2.1.1]hexane, bicyclo[2.2.1]heptane, bicyclo[3.1.1]heptane, bicyclo[2.2.2]octane, bicyclo[3.2.1]octane, preferably bicyclo[1.1.1]pentane and bicyclo[2.2.2]octane.

In some embodiments of a compound of formula III, X is O and Y is $C_{5-11}$ bridged bicycloalkyl. In some embodiments of a compound of formula III, X is O and Y is $C_{4-11}$ fused bicycloalkyl. In some embodiments of a compound of formula III, X is O and Y is $C_{5-11}$ spirocycloalkyl. In some embodiments of a compound of formula III, X is O and Y is selected from bicyclo[1.1.1]pentane, bicyclo[2.1.1]hexane, bicyclo[2.2.1]heptane, bicyclo[3.1.1]heptane, bicyclo[2.2.2]octane, bicyclo[3.2.1]octane, preferably bicyclo[1.1.1]pentane and bicyclo[2.2.2]octane.

In some embodiments of a compound of formula III, X is NH and Y is $C_{5-11}$ bridged bicycloalkyl. In some embodiments of a compound of formula III, X is NH and Y is $C_{4-11}$ fused bicycloalkyl. In some embodiments of a compound of formula III, X is NH and Y is $C_{5-11}$ spirocycloalkyl. In some embodiments of a compound of formula III, X is NH and Y is selected from bicyclo[1.1.1]pentane, bicyclo[2.1.1]hexane, bicyclo[2.2.1]heptane, bicyclo[3.1.1]heptane, bicyclo[2.2.2]octane, bicyclo[3.2.1]octane, preferably bicyclo[1.1.1]pentane and bicyclo[2.2.2]octane.

In some embodiments of a compound of formula III, Z is straight-chain or branched $C_{1-12}$ alkyl, wherein one or more $CH_2$ groups may independently be replaced by —($CH_2$—O—$CH_2$)—, —($CH_2$—$CH_2$—O)—, —(O—$CH_2$—$CH_2$)—, and —O—.

In some embodiments of a compound of formula III, Z is straight-chain or branched $C_{1-10}$ alkyl, wherein one or more $CH_2$ groups may independently be replaced by —($CH_2$—O—$CH_2$)—, —($CH_2$—$CH_2$—O)—, —(O—$CH_2$—$CH_2$)—.

In some embodiments of a compound of formula III, Z is straight-chain or branched $C_{1-8}$ alkyl, wherein up to five $CH_2$ groups may independently be replaced by —($CH_2$—O—$CH_2$)—, —($CH_2$—$CH_2$—O)—, —(O—$CH_2$—$CH_2$)—.

In some embodiments, the compound of the invention is of formula IV

IV

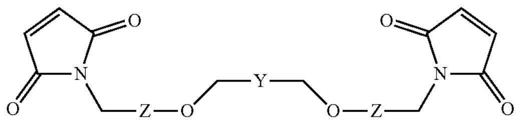

wherein

Y is a $C_{5-11}$ bridged bicycloalkyl,

Z is straight-chain or branched $C_{1-11}$ alkyl, wherein one or more $CH_2$ groups may independently be replaced by —($CH_2$—O—$CH_2$)—, —($CH_2$—$CH_2$—O)—, —(O—$CH_2$—$CH_2$)—, —O—, —NH—, and —NR—, wherein R is branched or linear $C_{1-6}$ alkyl.

In some embodiments of a compound of formula IV, Y is selected from bicyclo[1.1.1]pentane, bicyclo[2.1.1]hexane, bicyclo[2.2.1]heptane, bicyclo[3.1.1]heptane, bicyclo[2.2.2]octane, bicyclo[3.2.1]octane, preferably bicyclo[1.1.1]pentane and bicyclo[2.2.2]octane.

In some embodiments of a compound of formula IV, Z is straight-chain or branched $C_{1-11}$ alkyl, wherein one or more $CH_2$ groups may independently be replaced by —($CH_2$—O—$CH_2$)—, —($CH_2$—$CH_2$—O)—, —(O—$CH_2$—$CH_2$)—, and —O—.

In some embodiments of a compound of formula IV, Z is straight-chain or branched $C_{1-9}$ alkyl, wherein one or more $CH_2$ groups may independently be replaced by —($CH_2$—O—$CH_2$)—, —($CH_2$—$CH_2$—O)—, —(O—$CH_2$—$CH_2$)—.

In some embodiments of a compound of formula IV, Z is straight-chain or branched $C_{1-7}$ alkyl, wherein up to five $CH_2$ groups may independently be replaced by —($CH_2$—O—$CH_2$)—, —($CH_2$—$CH_2$—O)—, —(O—$CH_2$—$CH_2$)—.

In some embodiments of a compound of formula IV, Y is selected from bicyclo[1.1.1]pentane, bicyclo[2.1.1]hexane, bicyclo[2.2.1]heptane, bicyclo[3.1.1]heptane, bicyclo[2.2.2]octane, bicyclo[3.2.1]octane, and Z is straight-chain or branched $C_{1-9}$ alkyl, wherein one or more $CH_2$ groups may independently be replaced by —($CH_2$—O—$CH_2$)—, —($CH_2$—$CH_2$—O)—, —(O—$CH_2$—$CH_2$)—.

In some embodiments of a compound of formula IV, Y is bicyclo[1.1.1]pentane and Z is straight-chain or branched $C_{1-9}$ alkyl, wherein one or more $CH_2$ groups may independently be replaced by —($CH_2$—O—$CH_2$)—, —($CH_2$—$CH_2$—O)—, —(O—$CH_2$—$CH_2$)—.

In some embodiments, the compound of the invention is of formula V

V

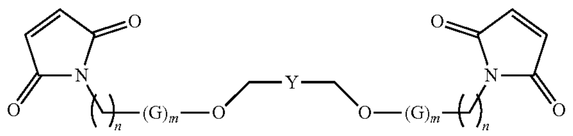

wherein

Y is a $C_{5-11}$ bridged bicycloalkyl,

G is —($CH_2$—O—$CH_2$)—, —($CH_2$—$CH_2$—O)—, —(O—$CH_2$—$CH_2$)—, n is 1 to 4, preferably 2 or 3, and m is 0 to 8, preferably 0 to 3.

In some embodiments of a compound of formula V, Y is selected from bicyclo[1.1.1]pentane, bicyclo[2.1.1]hexane, bicyclo[2.2.1]heptane, bicyclo[3.1.1]heptane, bicyclo[2.2.2]octane, bicyclo[3.2.1]octane, preferably bicyclo[1.1.1]pentane and bicyclo[2.2.2]octane.

In some embodiments of a compound of formula V, G is —($CH_2$—O—$CH_2$)—. In some embodiments of a compound of formula V, G is —($CH_2$—$CH_2$—O)—. In some embodiments of a compound of formula V, G is —(O—$CH_2$—$CH_2$)—.

In some embodiments of a compound of formula V, n is 1. In some embodiments of a compound of formula V, n is 2. In some embodiments of a compound of formula V, n is 3. In some embodiments of a compound of formula V, n is 4.

In some embodiments of a compound of formula V, m is 0. In some embodiments of a compound of formula V, m is 1. In some embodiments of a compound of formula V, m is 2. In some embodiments of a compound of formula V, m is 3. In some embodiments of a compound of formula V, m is 4. In some embodiments of a compound of formula V, m is 5. In some embodiments of a compound of formula V, m is 6. In some embodiments of a compound of formula V, m is 7. In some embodiments of a compound of formula V, m is 8.

In some embodiments of a compound of formula V, n is 2 and m is 0. In some embodiments of a compound of formula V, n is 2 and m is 1. In some embodiments of a compound of formula V, n is 2 and m is 2. In some embodiments of a compound of formula V, n is 2 and m is 3.

In some embodiments of a compound of formula V, n is 3 and m is 0. In some embodiments of a compound of formula V, n is 3 and m is 1. In some embodiments of a compound of formula V, n is 3 and m is 2. In some embodiments of a compound of formula V, n is 3 and m is 3.

In further specific embodiments, the disclosure is directed to the specific examples disclosed in Table 1.

TABLE 1

| | |
|---|---|
| 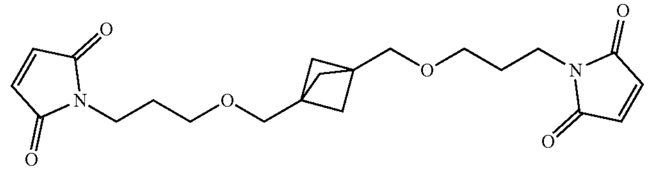 [SMILES: O=C1C=CC(=O)N1CCCOCC12CC(COCCCN3C(=O)C=CC3=O)(C1)C2] | SPC-TB-0001 |
| 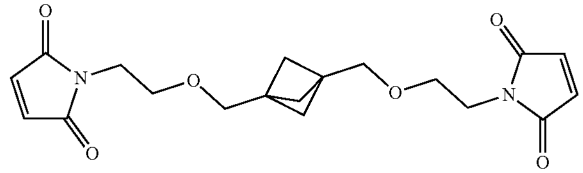 [SMILES: O=C1C=CC(=O)N1CCOCC12CC(COCCN3C(=O)C=CC3=O)(C1)C2] | SPC-TB-0002 |
| 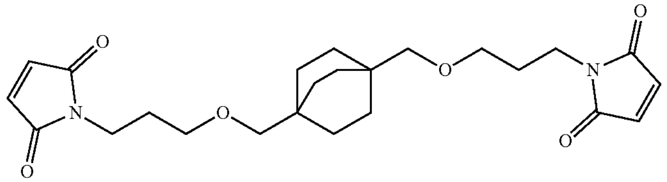 [SMILES: O=C1C=CC(=O)N1CCCOCC12CCC(COCCCN3C(=O)C=CC3=O)(CC1)CC2] | SPC-TB-0003 |
| 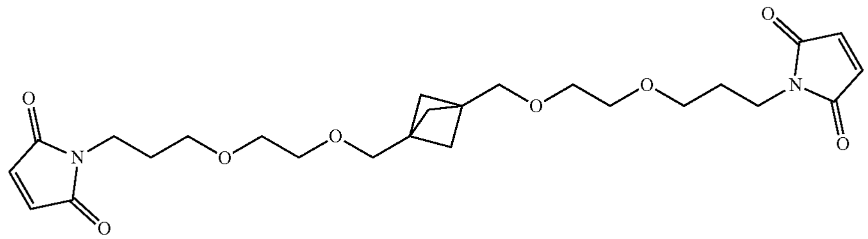 [SMILES: O=C1C=CC(=O)N1CCCOCCOCC12CC(COCCOCCCN3C(=O)C=CC3=O)(C1)C2] | SPC-TB-0005 |
| 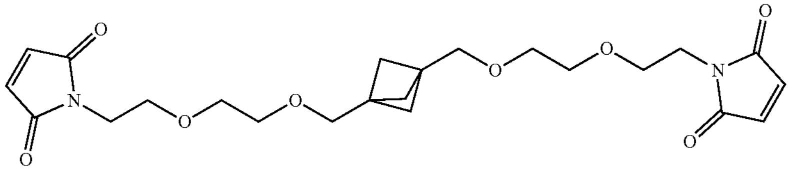 [SMILES: O=C1C=CC(=O)N1CCOCCOCC12CC(COCCOCCN3C(=O)C=CC3=O)(C1)C2] | SPC-TB-0007 |
| 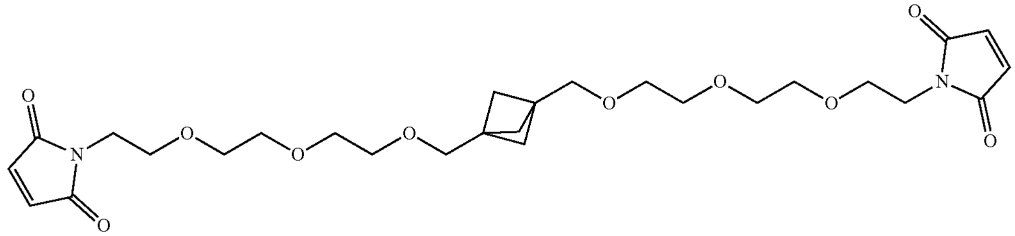 [SMILES: O=C1C=CC(=O)N1CCOCCOCCOCC12CC(COCCOCCOCCN3C(=O)C=CC3=O)(C1)C2] | SPC-TB-0013 |
| 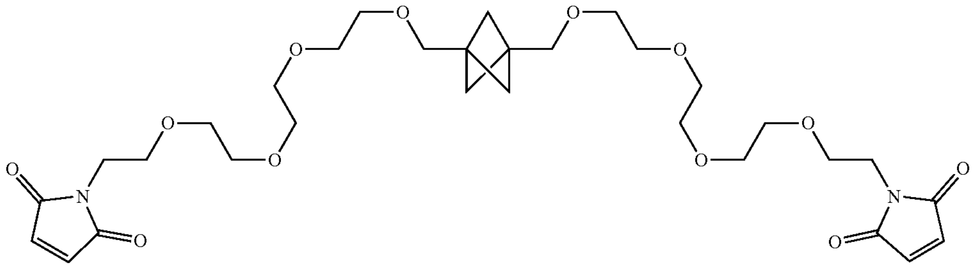 [SMILES: O=C1C=CC(=O)N1CCOCCOCCOCCOCC12CC(COCCOCCOCCOCCN3C(=O)C=CC3=O)(C1)C2] | SPC-TB-0014 |

In some embodiments, the disclosure is directed to the (S) enantiomer of the compounds of any of formula I-V. In some embodiments, the disclosure is directed to the (R) enantiomer of the compounds of any of formula I-V. In some embodiments, the disclosure is directed to the racemate of the compounds of any of formula I-V.

The compounds of the disclosure may contain one or more asymmetric centers in the molecule. A compound without designation of the stereochemistry is to be understood to include all the optical isomers (e.g., diastereomers, enantiomers, etc.) in pure or substantially pure form, as well as mixtures thereof (e.g. a racemic mixture, or an enantiomerically enriched mixture). It is well known in the art how to prepare such optically active forms (e.g. by resolution of the racemic form by recrystallization techniques, by synthesis from optically-active starting materials, by chiral synthesis, by chromatographic separation using a chiral stationary phase, and other methods).

The compounds may be isotopically-labeled compounds, for example, compounds including various isotopes of hydrogen, carbon, nitrogen, oxygen. The disclosed compounds may exist in tautomeric forms and mixtures and separate individual tautomers are contemplated. In addition, some compounds may exhibit polymorphism.

The compounds of the disclosure include the free form as well as the pharmaceutically acceptable salts and stereoisomers thereof. The pharmaceutically acceptable salts include all the typical pharmaceutically acceptable salts. The pharmaceutically acceptable salts of the present compounds can be synthesized from the compounds of this disclosure which contain a basic or acidic moiety by conventional chemical methods, see e.g. Berge et al, "Pharmaceutical Salts," J. Pharm. ScL, 1977:66:1-19. Furthermore, the compounds of the disclosure also include lyophilized and polymorphs of the free form.

For example, conventional pharmaceutically acceptable salts for a basic compound include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Conventional pharmaceutically acceptable salts for an acidic compound include those derived from inorganic bases include aluminum, ammonium, calcium, copper, ferric, ferrous, lithium, magnesium, manganic salts, manganous, potassium, sodium, zinc and the like. Salts derived from pharmaceutically acceptable organic bases include salts of primary, secondary and tertiary amines, substituted amines including naturally occurring substituted amines, cyclic amines and basic ion exchange resins, such as arginine, betaine caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The compounds of the disclosure may exist in solid, i.e. crystalline (e.g., polymorphs, i.e., different crystalline structures that have the same chemical composition but differ in packing, geometrical arrangement) or noncrystalline form (optionally as solvates) or liquid form. In the solid state, it may exist in, or as a mixture thereof. In crystalline solvates, solvent molecules are incorporated into the crystalline lattice during crystallization. The formation of solvates may include non-aqueous solvents such as, but not limited to, ethanol, isopropanol, DMSO, acetic acid, ethanolamine, or ethyl acetate, or aqueous solvents such as water (also called "hydrates"). Different polymorphs may be produced, for example, by changing or adjusting the reaction conditions or reagents.

In a further aspect, the disclosure also provides methods of preparation of the compounds of formula I-V of the disclosure.

In yet another aspect, the disclosure further provides a cosmetic preparation comprising an effective amount of one or more of the compounds of the disclosure or pharmaceutically acceptable salt thereof and one or more pharmaceutically acceptable carriers and/or excipients (also referred to as diluents). The excipients are acceptable in the sense of being compatible with the other ingredients of the formulation and not deleterious to the recipient thereof. The term "effective amount" as used herein refers to the amount of a compound (as such or in form of a cosmetic preparation) of the present disclosure which is effective for producing the desired effect of hair repair.

Typically, the pH of the cosmetic preparation is 3.5-6, particularly 4-5 at 20° C. The pH may, for example, be adjusted using lactic acid, citric acid and the like.

Typically, the concentration of the compound disclosed herein will be between 0.01% and 5% by weight of the cosmetic preparation, such as 2%-4% by weight. In some embodiments, the concentration of the compound disclosed herein is 50-130 mmol per liter of the cosmetic preparation, particularly 80-100 mmol per liter.

In some embodiments, the cosmetic preparation comprises a solubilizer. The concentration of the solubilizer may, for example, be 5%-20% by weight of the cosmetic preparation, particularly 10%-20%, e.g. 15%-20%.

In some embodiments, the cosmetic preparation comprises phenoxyethanol at a concentration of 0.1%-1.7% by weight of the cosmetic preparation, particularly 0.7%-1.1%, e.g. 0.9%.

In some embodiments, the cosmetic preparation comprises ethylhexylglycerin at a concentration of 0.01%-0.2% by weight of the cosmetic preparation, particularly 0.08%-0.12%, e.g. 0.1%.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the person being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in cosmetic preparations.

Such compositions may contain further components conventional in cosmetic preparations, e.g. wetting agents, emulsifiers and lubricants, such as sodium lauryl sulfate and magnesium stearate, as well as coloring agents, release agents, coating agents, sweetening, flavoring and perfuming agents, preservatives and antioxidants, pH modifiers, bulking agents, and further active agents. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Such compositions may be prepared by any method known in the art, for example, by bringing into association the active ingredient with one or more carriers and/or excipients. Different compositions and examples of carriers and/or excipients are well known to the skilled person and are described in detail in, e.g., Remington: The Science and Practice of Pharmacy. Pharmaceutical Press, 2013; Rowe, Sheskey, Quinn: Handbook of Pharmaceutical Excipients. Pharmaceutical Press, 2009. Excipients that may be used in the preparation of the cosmetic preparations may include one or more of buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide a composition or preparation suitable for an administration of choice.

The cosmetic preparations of the disclosure may be in any suitable form. In some embodiments, such suitable forms include but are not limited to liquids, e.g. low to moderate viscosity liquids, such as lotions, milks, mousses, sprays, gels, creams, ointments, pastes and the like. Suitable excipients, such as those listed above, are included or excluded from the skin formulation depending on the form of use of the formulation (e.g., lotion, gel, ointment, or cream).

Liquid forms of the compounds of the disclosure include pharmaceutically acceptable emulsions, microemulsions, solutions, suspensions, syrups and elixirs. In addition to the active ingredient, the liquid forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. In form of suspensions, a compound may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In form of sprays, ointments, pastes, creams, lotions, gels, solutions, a compound may be mixed under sterile conditions with a pharmaceutically-acceptable carrier, and with any preservatives, buffers, or propellants which may be required. Such ointments, pastes, creams and gels may contain, in addition to a compound of the disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In form of powders and sprays, a compound of the disclosure, may contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

In some embodiments, the cosmetic preparations are hair care products, which includes products in form of a shampoo, a conditioner, a hair mask, a hair rinse, hair spray, hair foam, hair mousse, hair gel, hair tonic, and the like.

It is understood that all contemplated compositions and preparations must be stable under the conditions of manufacture and storage, and preserved against the contaminating action of microorganisms, such as bacteria and fungi.

The amounts of a compound of the disclosure in the cosmetic preparations of the disclosure may be adjusted in order to obtain an amount of a compound of the disclosure which is effective to achieve the desired cosmetic response for a particular person, composition, and mode of administration, without being deleterious to the person. The chosen amount will depend upon a variety of factors including the nature of the particular compound of the present disclosure used, the route of administration, the time of administration, the duration of the treatment, other compounds and/or materials used in combination with the particular compound, the age, sex, weight, condition, general health and prior medical history of the person being treated, and like factors well known in the medical arts.

Typically, a suitable amount of a compound of the disclosure will be that amount of the compound, which is the lowest amount effective to produce a desired effect. Such an effective dose will generally depend upon the factors described above. In form of shampoo, the amount of cosmetic preparation applied per treatment may, for example, be 1 g-10 g. In form of conditioner and/or hair mask, the amount of cosmetic preparation applied per treatment may, for example, be 1 g-10 g. In form of leave-on conditioner or leave-on mask, the amount of cosmetic preparation applied per treatment may, for example, be 0.1 g-7 g.

All of the compounds, compositions, preparations and/or methods disclosed and claimed herein can be made and executed without undue experimentation in light of the present disclosure. It will be apparent to those of skill in the art that variations may be applied to the present disclosure without departing from the scope of the disclosure. The Examples provided herein are intended to be illustrative and are not exhaustive; thus, the illustrated Examples should not be viewed as limiting the disclosure in any way.

EXAMPLES

Materials

N-Fmoc-cysteine (hereinafter C1) or N-Cbz-cysteine (hereinafter C2) were obtained by reduction of their cysteine counterparts via a literature known method. *Adv. Syn. Catal.*, 2020, 362, 5093-5104. DOI: 10.1002/adsc.202000716. "OLAPLEX® No. 0 Intensive Bond Building Hair Treatment" is a commercially available product which comprises an active agent, water, phenoxyethanol and sodium benzoate. The active agent is hereinafter labelled "Olaplex active agent" or "reference compound #2".

Example 1: Synthesis of Reference Compounds

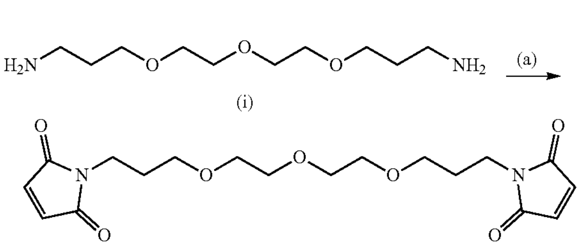

reference compound #1

(a) Reference Compound #1

To a solution of maleic anhydride (25.0 g, 5.00 Eq, 260 mol) in acetic acid (200 mL) was added 3,3'-((oxybis(ethane-2,1-diyl))bis(oxy))bis(propan-1-amine) (12.0 g, 1.00 Eq, 52.0 mmol) and refluxed for 2 h. The solution was allowed to cool to rt. Then toluene (50 mL) was added. The mixture was concentrated under reduced pressure to approximately 100 mL. It was filtered over a plug of silica (~3 cm) and washed with a 1/1-mixture of EtOAc/Cyclohexane. The crude material was purified by column chromatography (silica gel, EtOAc in Cyclohexane, gradient 0-80% EtOAc) to afford reference compound #1 as yellowish oil (3.4 g, 17%).

$^1H$ NMR (400 MHz, DMSO) δ 6.99 (s, 4H), 3.50-3.40 (m, 12H), 3.37 (t, J=6.1 Hz, 4H), 1.70 (m, 4H). LC-MS (ESI+), $[M+H]^+$=381.

(b) Reference Compound #2=Olaplex Active Agent

The active agent "Olaplex active agent", which was used as a test substrate #2 in example 8, has the following structure:

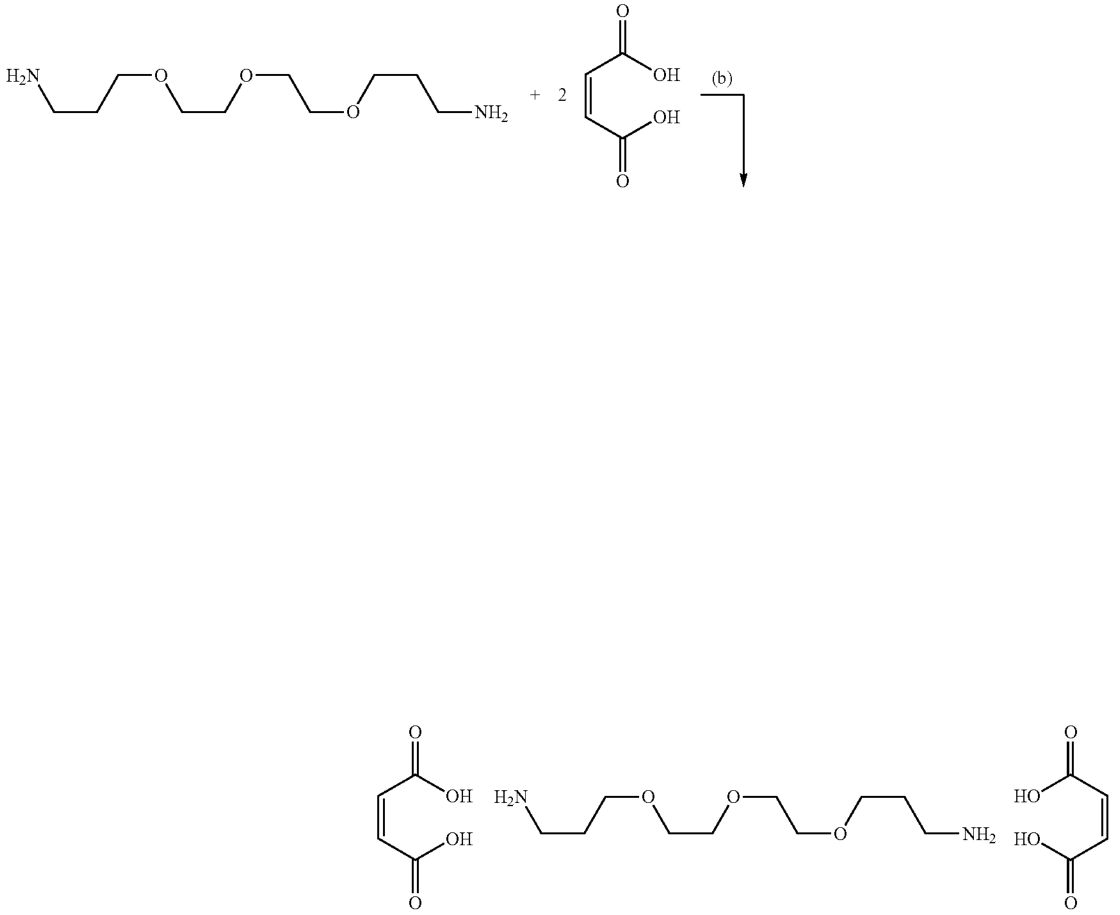

Olaplex active agent =
reference compound #2

It was synthesized by reacting 2 equivalents of the corresponding acid with 1 equivalent of the corresponding diamine.

Example 2: Synthesis of Compound 1 (SPC-TB-0001)

added 40% tetrabutylammonium hydroxide solution in water (40.0 mL, 1.20 Eq, 61.0 mmol) at rt. Then acrylonitrile (7.90 mL, 4.00 Eq, 210 mmol) was added dropwise and the biphasic mixture was vigorously stirred at rt for 4 h. Afterwards the phases were separated and the aqueous phase was extracted with EtOAc (3×). The combined organic phases were washed with brine (1×), dried over sodium sulfate, Scheme method 1-A

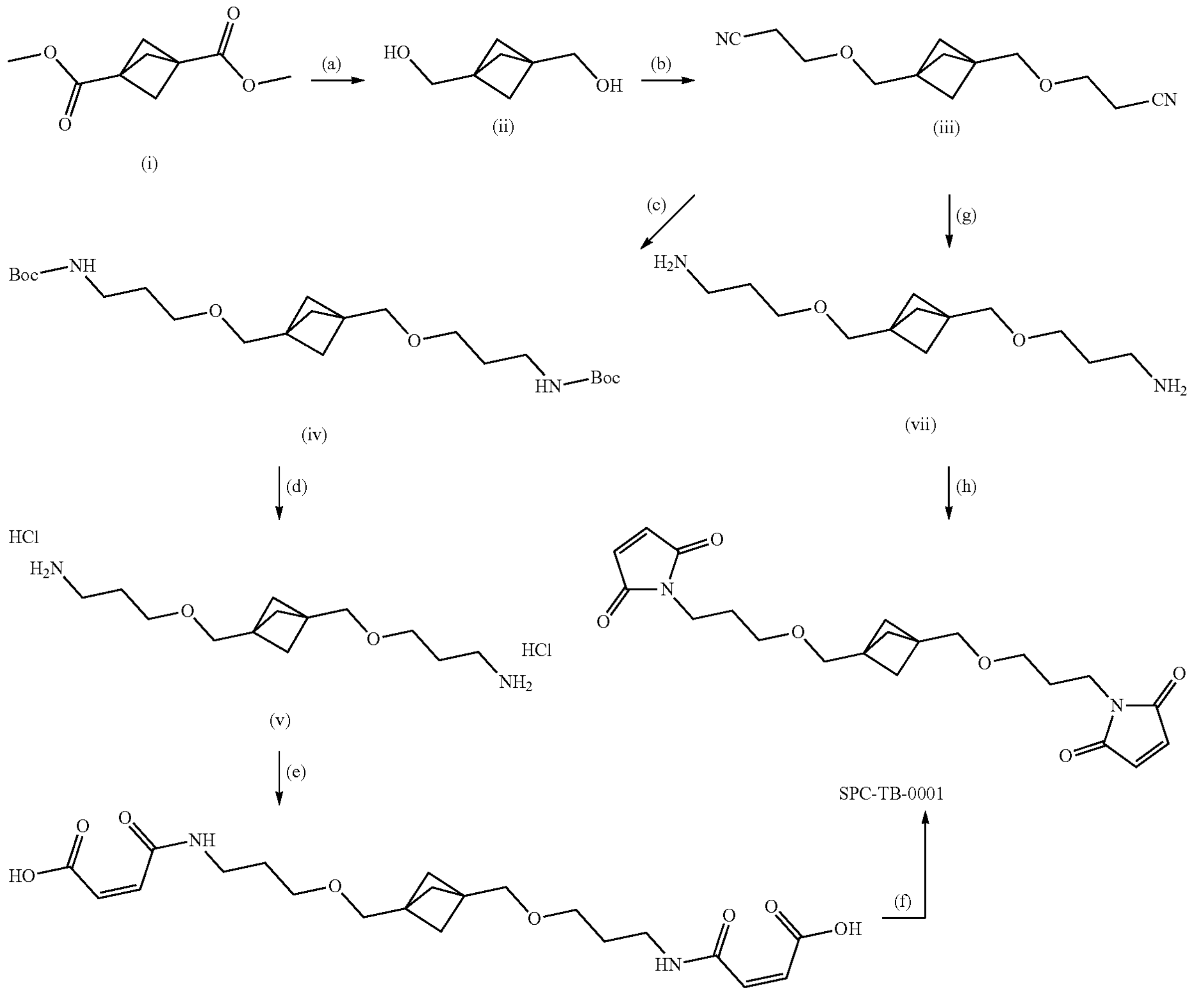

(i) (ii) (iii) (iv) (vii) (v) SPC-TB-0001 (vi)

(a) Bis-Alcohol (ii)

To suspension of dimethyl bicyclo[1.1.1]pentane-1,3-dicarboxylate (25.38 g, 1.00 Eq, 137.8 mmol) at 0° C. in anhydrous THF (551 mL) under nitrogen was added dropwise a 2-M solution of $LiAlH_4$ in THF (151.6 mL, 2.20 Eq, 303.1 mmol). Maintain temperature below 10° C. in flask while adding. The resulting solution was stirred at rt for 16 h. After completion it was quenched by performing a Fieser work-up. The crude material (19.08 g, quant. yield) was isolated as colorless oil which solidified after a while. It was used further without purification.

$^1$H NMR (400 MHz, DMSO) δ 4.39 (t, J=5.6 Hz, 2H), 3.35 (d, J=5.6 Hz, 4H), 1.45 (s, 6H)

(b) Bis-Cyano Intermediate (iii)

To a solution of bicyclo[1.1.1]pentane-1,3-diyldimethanol (6.60 g, 1.00 Eq, 51.0 mmol) in toluene (40.0 mL) was filtered and concentrated under reduced pressure. The crude material was purified by column chromatography (silica gel, EtOAc in Cyclohexane, gradient 0-100% EtOAc) to afford the title compound as colorless oil (9.2 g, 76%).

$^1$H NMR (400 MHz, DMSO) δ 3.57 (t, J=6.0 Hz, 4H), 3.43 (s, 4H), 2.73 (t, J=6.0 Hz, 4H), 1.62 (s, 6H). TLC-MS, $[M+H]^+=235$ (c) Bis-Boc-Protected-Amine-Intermediate (iv)

To a solution of 3,3'-((bicyclo[1.1.1]pentane-1,3-diylbis(methylene))bis(oxy))dipropanenitrile (413 mg, 1.00 Eq, 1.76 mmol) and Nickel(II) chloride-hexaquocomplex (545 mg, 1.30 Eq, 2.29 mmol) in MeOH (35 mL) at 0° C. was added $NaBH_4$ (533 mg, 8.00 Eq, 14.1 mmol) portionwise. The black reaction mixture was stirred for 30 min then Boc-Anhydride (1.15 g, 3.00 Eq, 5.29 mmol) was added and allowed to warm up to rt for 14 h. The reaction was quenched with brine (1 mL), the methanol was removed under reduced pressure and the residue was taken up again in diethyl ether (150 mL). The mixture was filtered over a plug of celite (2 cm) and washed down with diethyl ether (3×50 mL). The organic phase was washed with water (100 mL) and brine (100 mL) and concentrated under reduced pressure. The crude material (550 mg, 70%) was afforded as yellow oil and used further without purification. Note: product contained Boc-Anhydride.

$^1$H NMR (400 MHz, DMSO) δ 6.72 (s, 2H), 3.37 (t, J=6.3 Hz, 4H), 3.33 (s, 4H), 2.96 (td, J=7.0, 5.7 Hz, 4H), 1.58 (s, 6H), 1.37 (m, 21H). TLC-MS, $[M+H]^+$=443

(d) Bis-Amine-Hydrochloride-Intermediate (v)

di-tert-butyl(((bicyclo[1.1.1]pentane-1,3-diylbis(methylene))bis(oxy))bis(propane-3,1-diyl))dicarbamate (550 mg, 1.00 Eq, 1.24 mmol) was dissolved in 4-M HCl in dioxane (3.11 mL, 10.0 Eq, 12.4 mmol) and stirred at rt for 16 h. The reaction mixture was concentrated. The residue was triturated with diethyl ether (5 mL). The title compound was afforded as white solid (401 mg, quant. yield) and was used further without purification.

$^1$H NMR (400 MHz, DMSO) δ 8.02 (s, 4H), 7.51-7.10 (m, 1H), 3.44 (t, J=9.0 Hz, 4H), 3.36 (s, 4H), 2.80 (m, 4H), 1.59 (s, 6H). TLC-MS, $[M+H]^+$=243

(e) Bis-Acid-Intermediate (vi)

A suspension of 3,3'-((bicyclo[1.1.1]pentane-1,3-diylbis(methylene))bis(oxy))bis(propan-1-amine)dihydrochloride (350 mg, 1.00 Eq, 1.11 mmol) and TEA (0.51 mL, 3.30 Eq, 3.66 mmol) is cooled to 0° C. Then maleic anhydride (359 mg, 3.30 Eq, 3.66 mmol) as added. The mixture is allowed to warm-up to rt for 16 h. Then water is added and the mixture is acidified to pH=2 with 2M HCl-solution. The aqueous phase is extracted with EtOAc (6×). The combined organic phases are dried over sodium sulfate, filtered and concentrated to dryness. The crude material was afforded as colorless oil (360 mg, 74%) and was used without further purification.

$^1$H NMR (400 MHz, DMSO) δ 9.06 (s, 2H), 6.45-6.33 (m, 2H), 6.23 (d, J=12.5 Hz, 2H), 3.41 (t, J=6.2 Hz, 4H), 3.35 (s, 4H), 3.22 (td, J=7.0, 5.6 Hz, 4H), 1.69 (t, J=6.6 Hz, 4H), 1.58 (s, 6H). LC-MS (ESI+), $[M+H]^+$=439, $[M-H]^-$=437

(f) SPC-TB-0001

To a solution of (2Z,2'Z)-4,4'-((((bicyclo[1.1.1]pentane-1,3-diylbis(methylene))bis(oxy))bis(propane-3,1-diyl))bis(azanediyl))bis(4-oxobut-2-enoic acid) (360 mg, 1.00 Eq, 821 μmol) in Acetone (5.5 mL) was added sodium acetate (54.0 mg, 0.80 Eq, 657 μmol). The mixture was refluxed for 16 h under normal atmosphere. Then the reaction mixture was allowed to cool to rt and diluted with EtOAc. The organic phase was washed with saturated $NaHCO_3$-solution (1×), dried over sodium sulfate, filtered and concentrated to dryness affording a thick brown oil. The crude material was purified by column chromatography (silica gel, EtOAc in Cyclohexane, gradient 0-60% EtOAc) to afford the desired product as yellowish oil which solidified (37 mg, 11%).

$^1$H NMR (400 MHz, DMSO) δ 7.00 (s, 4H), 3.46 (t, J=6.9 Hz, 4H), 3.35 (t, J=6.0 Hz, 4H), 3.28 (s, 4H), 1.74-1.66 (m, 4H), 1.53 (s, 6H). TLC-MS, $[M+H]^+$=403

(g) Bis-Amine-Intermediate (vii)

3,3'-((bicyclo[1.1.1]pentane-1,3-diylbis(methylene))bis(oxy))dipropanenitrile was prepared according to steps (a) and (b) of Scheme Method 1. To a suspension of 3,3'-((bicyclo[1.1.1]pentane-1,3-diylbis(methylene))bis(oxy))dipropanenitrile (10.3 g, 1.00 Eq, 44.0 mmol) in THF (393 mL) was slowly added 1-M $BH_3$*THF-solution in THF (220 mL, 5.00 Eq, 220 mmol) at ° C. under nitrogen. The solution was stirred for 1 h at 0° C. and 1 h at reflux. The reaction mixture was cooled to 0° C. and MeOH (126 mL) was added dropwise followed by 37%-HCl (15.8 mL, 1.00 Eq, 44.0 mmol). Then the reaction mixture was allowed to warm-up to rt. Solvent was removed under reduced pressure (200 mbar, 40° C.). Residue was basified with 2M NaOH and extracted with EtOAc (3×). Combined org. phases were washed with brine, dried over $MgSO_4$, filtered and concentrated under reduced pressure. Crude material was directly without purification (11.5 g, quant).

TLC-MS, $[M+H]^+$=243

(h) SPC-TB-0001

3,3'-((bicyclo[1.1.1]pentane-1,3-diylbis(methylene))bis(oxy))bis(propan-1-amine) (840 mg, 1.00 Eq, 3.47 mmol) was suspended in sat. sodium bicarbonate solution (26.7 mL). Mixture is cooled to 0° C. after which methyl 2,5-dioxo-2,5-dihydro-1H-pyrrole-1-carboxylate (v-2) (1.08 g, 2.00 Eq, 6.93 mmol) is added. Yellow suspension was stirred at 0° C. for 2 h. The aq. phase was extracted with DCM (3×). The combined org. phases were washed with brine (1×) and concentrated. The crude material was purified by column chromatography (silica gel, EtOAc in cyclohexane up to 100% EtOAc) to afford the title compound was white solid (294 mg, 21%).

$^1$H NMR (400 MHz, DMSO) δ 7.00 (s, 4H), 3.46 (t, J=6.9 Hz, 4H), 3.35 (t, J=6.0 Hz, 4H), 3.28 (s, 4H), 1.74-1.66 (m, 4H), 1.53 (s, 6H). NMR was in agreement with spectrum from method 1. TLC-MS, $[M+H]^+$=403

Example 3: Synthesis of Compound 2 (SPC-TB-0002)

Scheme method 2

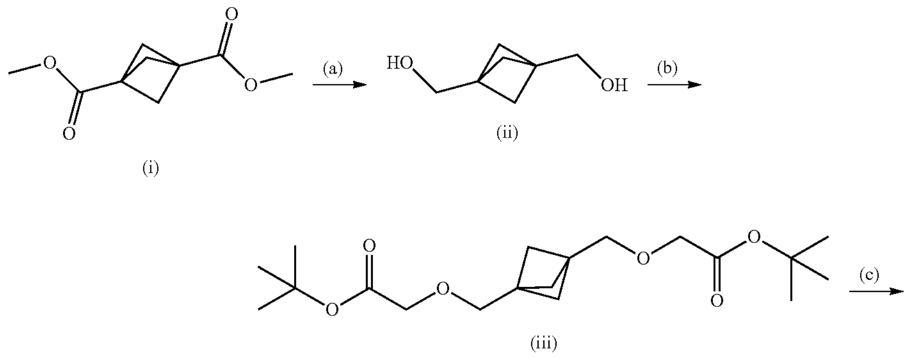

(i) (ii) (iii)

-continued

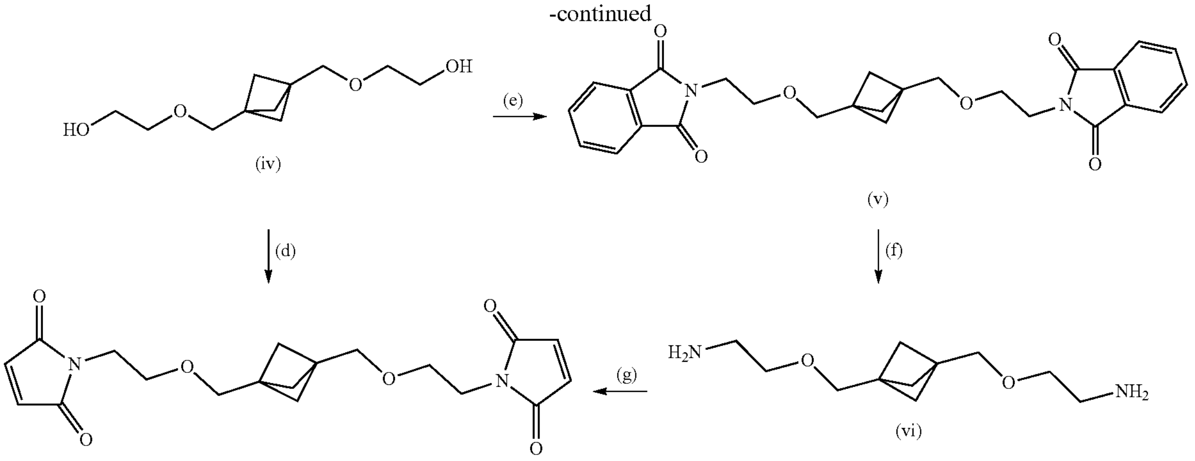

SPC-TB-0002

(a)—Synthesis of bicyclo[1.1.1]pentane-1,3-diyldimethanol (ii)

To a solution of dimethyl bicyclo[1.1.1]pentane-1,3-dicarboxylate (25.38 g, 1 eq., 137.8 mmol) at 0° C. in anhydrous THF (551 mL) under nitrogen was added dropwise a 2M solution of $LiAlH_4$ in THF (151.6 mL, 2.2 eq., 303.1 mmol). Temperature is maintained below 10° C. in the flask during the addition. The reaction mixture was stirred at rt. for 16 h. After reaction completion, Fieser work-up was performed to afford the desired product bicyclo[1.1.1]pentane-1,3-diyldimethanol (19.08 g, 148.9 mmol, quant.) as a transparent oil that solidified on standing.

$^1$H NMR (400 MHz, DMSO) δ 4.39 (t, J=5.6 Hz, 2H), 3.35 (d, J=5.6 Hz, 4H), 1.45 (s, 6H). TLC (60% EtOAc/cyclohexane). Rf product 0.2. $KMNO_4$ stain.

(b) Synthesis of di-tert-butyl 2,2'-((bicyclo[1.1.1]pentane-1,3-diylbis(methylene))bis(oxy))diacetate (iii)

To a solution of bicyclo[1.1.1]pentane-1,3-diyldimethanol (500 mg, 1 eq., 3.90 mmol) and tetrabutylammonium bromide (717 mg, 0.57 eq., 2.22 mmol) in 50% aq. NaOH solution (24 mL) and toluene (12 mL) in a 2:1 ratio was added tert-butyl 2-bromoacetate (6.09 g, 4.64 mL, 8 eq., 31.2 mmol). The reaction mixture was stirred vigorously at rt. for 16 h. After reaction completion, water and EtOAc were added and the layers were separated. The aqueous layer was extracted with EtOAc (3×). Then, the combined organic layers were washed with brine, dried over anhydrous $MgSO_4$, and concentrated under vacuum. The residue was chromatographed (0% to 40% EtOAc/cyclohexane) to afford the desired product di-tert-butyl 2,2'-((bicyclo[1.1.1]pentane-1,3-diylbis(methylene))bis(oxy))diacetate (900 mg, 2.52 mmol, 64.7%) as a white solid.

$^1$H NMR (400 MHz, $CDCl_3$) δ 3.96 (s, 4H), 3.53 (s, 4H), 1.73 (s, 6H), 1.47 (s, 18H). TLC (20% EtOAc/cyclohexane). Rf product 0.5. CAM/p-anisaldehyde stain. TLC-MS: $[M+H]^+$=244 (minus the two t-Bu groups).

(c) Synthesis of 2,2'-((bicyclo[1.1.1]pentane-1,3-diylbis(methylene))bis(oxy))bis(ethan-1-ol) (iv)

To a solution of di-tert-butyl 2,2'-((bicyclo[1.1.1]pentane-1,3-diylbis(methylene))bis(oxy))diacetate (860 mg, 1 eq., 2.41 mmol) at 0° C. in anhydrous THF (12.1 mL) under nitrogen was added dropwise a 2M solution of $LiAlH_4$ in THF (201 mg, 2.65 mL, 2.00 molar, 2.2 eq., 5.31 mmol). The reaction mixture was stirred at rt. for 2 h. After reaction completion, Fieser work-up was performed to afford the desired product 2,2'-((bicyclo[1.1.1]pentane-1,3-diylbis(methylene))bis(oxy))bis(ethan-1-ol) (420 mg, 1.94 mmol, 80.5%) as a transparent oil.

$^1$H NMR (400 MHz, DMSO) δ 4.54 (t, J=5.4 Hz, 2H), 3.47 (tdd, J=6.1, 5.2, 1.1 Hz, 4H), 3.40-3.36 (m, 8H), 1.58 (s, 6H). TLC (50% EtOAc/cyclohexane). Rf product 0.1. CAM/p-anisaldehyde stain. Not UV active.

(d) Synthesis of 1,1'-(((bicyclo[1.1.1]pentane-1,3-diylbis(methylene))bis(oxy))bis(ethane-2,1-diyl))bis(1H-pyrrole-2,5-dione)-(SPC-TB-0002)

To a solution in a microwave vial tube with triphenylphosphine (273 mg, 2.25 eq., 1.04 mmol) in anhydrous THF (2.89 mL), cooled to to 0° C. under nitrogen, was added DIAD (210 mg, 202 µL, 2.25 eq., 1.04 mmol) slowly dropwise over 5 min. The yellow reaction mixture was stirred for 5 min at 0° C. Then, 2,2'((bicyclo[1.1.1]pentane-1,3-diylbis(methylene))bis(oxy))bis(ethan-1-ol) (100 mg, 1 eq., 462 µmol) in THF (2.89 mL) was added stirred for 5 min at 0° C. again. Lastly, maleimide (108 mg, 2.40 eq., 1.11 mmol) was added and the resulting reaction mixture was allowed to warm up to rt. after 5 min and was stirred for 16 h at ambient temperature. After reaction completion, the reaction mixture was concentrated and the residue was chromatographed (0% to 80% EtOAc/cyclohexane) to afford the desired product 1,1'-(((bicyclo[1.1.1]pentane-1,3-diylbis(methylene))bis(oxy))bis(ethane-2,1-diyl))bis(1H-pyrrole-2,5-dione) (80.0 mg, 214 µmol, 46.2%) as a white solid.

$^1$H NMR (400 MHz, DMSO) δ 7.03 (s, 4H), 3.61-3.49 (m, 4H), 3.51-3.42 (m, 4H), 3.31 (s, 4H), 1.44 (s, 6H). TLC (80% EtOAc/cyclohexane). Rf product 0.75. $KMNO_4$ stain. Slightly UV active. TLC-MS: $[M+H]^+$=375.

(e) Synthesis of 2,2'-(((bicyclo[1.1.1]pentane-1,3-diylbis(methylene))bis(oxy))bis(ethane-2,1-diyl))bis(isoindoline-1,3-dione) (v)

To a solution in a microwave vial tube triphenylphosphine (225 mg, 3.25 eq., 857 µmol) in anhydrous THF (1.65 mL), cooled to to 0° C. under nitrogen, was added DIAD (173 mg, 167 µL, 3.25 eq., 857 µmol) slowly dropwise over 5 min. The yellow reaction mixture was stirred for 5 min at 0° C. Then, 2,2'-((bicyclo[1.1.1]pentane-1,3-diylbis(methylene))bis(oxy))bis(ethan-1-ol) (57.0 mg, 1 eq., 264 µmol) in THF (1.65 mL) was added stirred for 5 min at 0° C. again. Lastly, isoindoline-1,3-dione (132 mg, 3.40 eq., 896 µmol) was added and the resulting reaction mixture was allowed to warm up to rt. after 5 min and was stirred for 48 h at ambient temperature. After reaction completion, the reaction mixture was concentrated and the residue was chromatographed (0% to 40% EtOAc/cyclohexane) to afford the desired product 2,2'-(((bicyclo[1.1.1]pentane-1,3-diylbis(methylene))bis(oxy))bis(ethane-2,1-diyl))bis(isoindoline-1,3-dione) (108 mg, 228 μmol, 86.4%) as a transparent oil that solidified into a white solid on standing.

$^1$H NMR (400 MHz, $CDCl_3$) δ 7.89-7.80 (m, 4H), 7.76-7.66 (m, 4H), 3.86 (t, J=5.9 Hz, 4H), 3.65 (t, J=5.9 Hz, 4H), 3.40 (s, 4H), 1.52 (s, 6H). TLC (30% EtOAc/cyclohexane). Rf product 0.25. CAM stain. UV active. TLC-MS: $[M+H]^+$=475.

(f) Synthesis of 2,2'-((bicyclo[1.1.1]pentane-1,3-diylbis(methylene))bis(oxy))bis(ethan-1-amine)—(vi)

To a solution of 2,2'-(((bicyclo[1.1.1]pentane-1,3-diylbis(methylene))bis(oxy))bis(ethane-2,1-diyl))bis(isoindoline-1,3-dione) (108 mg, 1 eq., 228 μmol) in ethanol (7.59 mL) was added hydrazine hydrate (45.6 mg, 44.3 μL, 4 eq., 910 μmol). The reaction mixture was heated 50° C. and stirred for 16 h. Note: White precipitate crashes out after 1 h. After reaction completion, the white solid is removed via filtration and the filtrate is concentrated to afford the desired product 2,2'-((bicyclo[1.1.1]pentane-1,3-diylbis(methylene))bis(oxy))bis(ethan-1-amine) (95 mg, 0.44 mmol, quant.) as a white solid. The crude product is used in the next step without any further purification.

$^1$H NMR (400 MHz, DMSO) δ 3.36 (s, 4H), 3.33 (t, J=5.9 Hz, 4H), 2.62 (t, J=5.9 Hz, 4H), 1.59 (s, 4H). Do not observe amine protons. TLC (10% MeOH/DCM). Rf product baseline. Ninhydrin stain. Not UV active.

(g) Synthesis of 1,1'-(((bicyclo[1.1.1]pentane-1,3-diylbis(methylene))bis(oxy))bis(ethane-2,1-diyl))bis(1H-pyrrole-2,5-dione) (SPC-TB-0002)

To a solution of 2,2'-((bicyclo[1.1.1]pentane-1,3-diylbis(methylene))bis(oxy))bis(ethan-1-amine) (95.0 mg, 1 eq., 443 μmol) in acetic acid (2.46 mL) was added furan-2,5-dione (217 mg, 5 eq., 2.22 mmol) and the reaction mixture was refluxed at 125° C. for 4 h with stirring. After reaction completion, the acetic acid was co-evaporated or concentrated with toluene. The residue was chromatographed (0% to 80% EtOAc/cyclohexane) 1,1'-(((bicyclo[1.1.1]pentane-1,3-diylbis(methylene))bis(oxy))bis(ethane-2,1-diyl))bis(1H-pyrrole-2,5-dione) (29 mg, 77 μmol, 17%) as a white solid.

$^1$H NMR (400 MHz, DMSO) δ 7.03 (s, 4H), 3.59-3.51 (m, 4H), 3.47 (dd, J=5.9, 4.7 Hz, 4H), 3.31 (s, 4H), 1.44 (s, 6H). TLC (80% EtOAc/cyclohexane). Rf product 0.75. $KMNO_4$ stain. Sightly UV active. TLC-MS: $[M+H]^+$=375.

A. Example 4: Synthesis of Compound 3 (SPC-TB-0003)

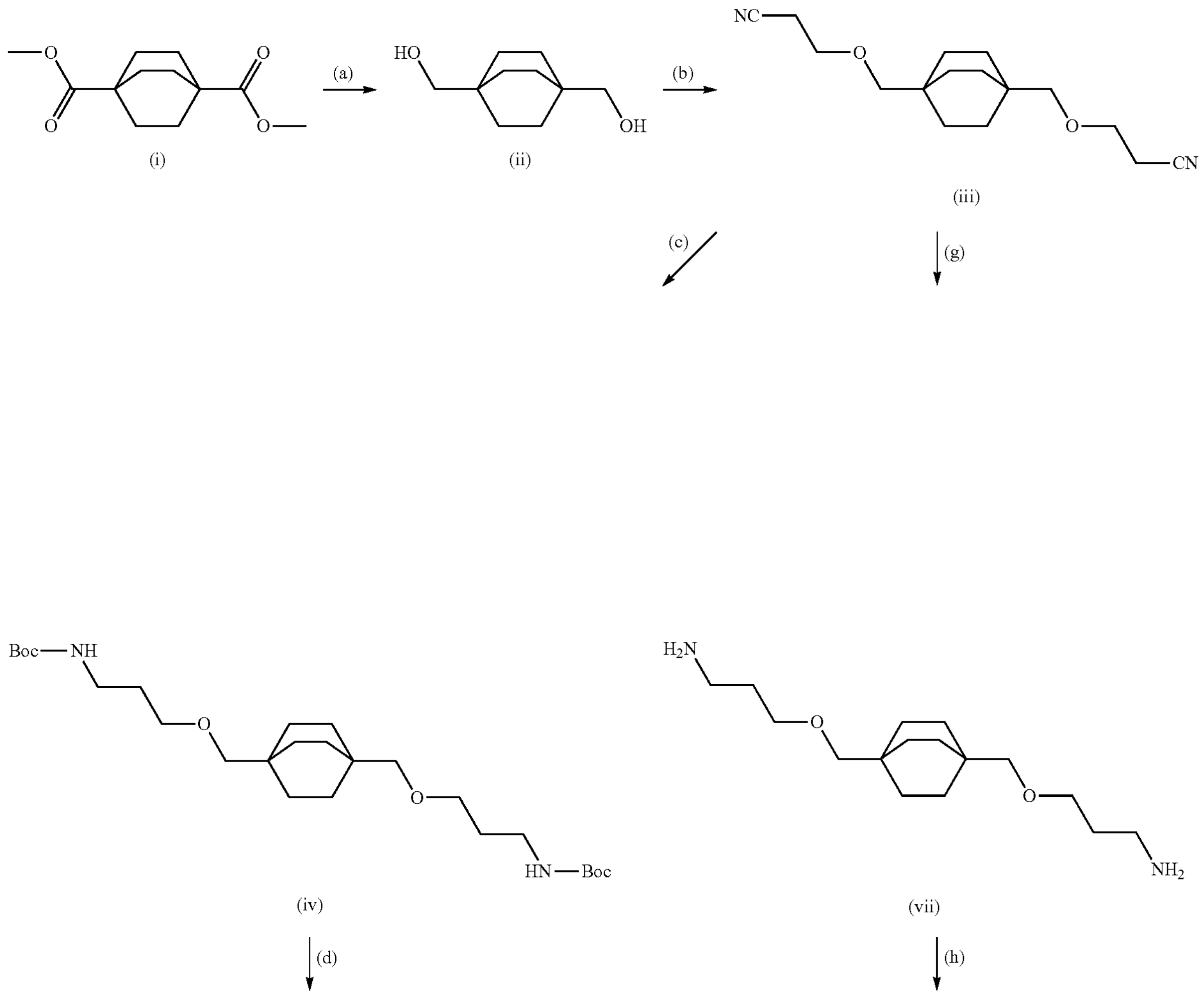

(i) (ii) (iii) (iv) (vii)

-continued

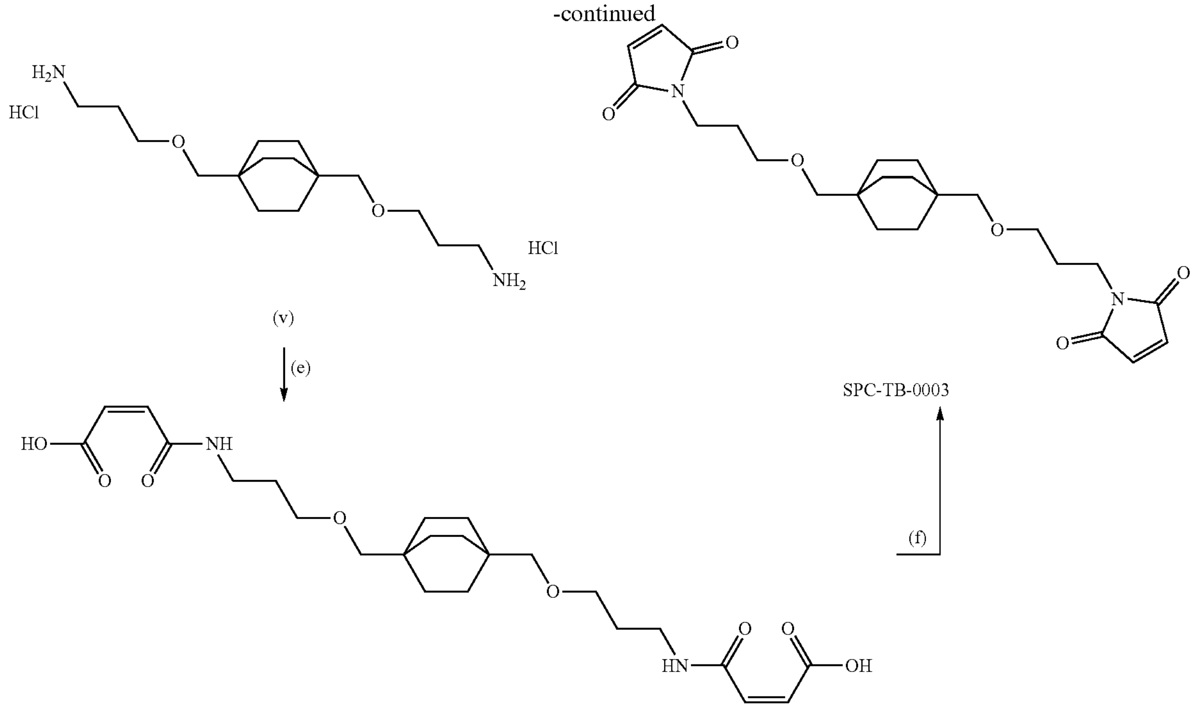

(vi)

(a) Bis-Alcohol Intermediate (ii).

A solution of 2M $LiAlH_4$ in THF (55 mL, 2.50 Eq, 0.11 mol) was cooled to 0° C. under nitrogen. Then a solution of dimethyl bicyclo[2.2.2]octane-1,4-dicarboxylate (10 g, 1.00 Eq, 44 mmol) in THF (100 mL) was added dropwise over the course of 1 hour. Temperature in flask was kept <10° C. during addition. After completion of addition the solution was stirred at 0° C. for 30 min. Afterwards the reaction was quenched by a performing a Fieser work-up. The crude material was isolated as colorless oil which solidified overnight (7.4 g, 98%) and was used further without purification.

$^1$H NMR (400 MHz, DMSO) δ 4.24 (t, J=5.5 Hz, 2H), 3.01 (d, J=5.5 Hz, 4H), 1.29 (s, 12H).

(b) Bis-Cyano-Intermediate (iii)

To a solution of bicyclo[2.2.2]octane-1,4-diyldimethanol (1.0 g, 1.00 Eq, 6.00 mmol) in 0.5-M NaOH (6 mL) and 1,4-dioxane (6 mL) was added acrylonitrile (1.40 mL, 6.00 Eq, 36.0 mmol). The solution was stirred at rt for 22 h and at 50° C. for 2 h. After cooled down to rt DCM (30 mL) was added into the mixture and the phases were separated. The organic phase was washed with brine (2×20 mL), dried over sodium sulfate, filtered and concentrated under reduced pressure. The crude material was purified by column chromatography (silica gel, EtOAc in Cyclohexane, gradient 0-40% EtOAc) to afford the desired product as colorless oil which solidified (560 mg, 30%).

$^1$H NMR (400 MHz, $CDCl_3$) δ 3.60 (t, J=6.4 Hz, 4H), 3.09 (s, 4H), 2.57 (t, J=6.4 Hz, 4H), 1.42 (s, 12H). TLC-MS: $[M+H]^+$=277

(c) Bis-Boc-Protected-Amine-Intermediate (iv)

To a solution of 3,3'-((bicyclo[2.2.2]octane-1,4-diylbis(methylene))bis(oxy))dipropanenitrile (560 mg, 1.00 Eq, 2.03 mmol) and Nickel(II) chloride-hexahydrate (626 mg, 1.3 Eq, 2.63 mmol) in MeOH (40.5 mL) at 0° C. was added $NaBH_4$ (613 mg, 8.00 Eq, 16.2 mmol) portionwise. The black mixture is stirred at 0° C. for 2 h then Boc-anhydride (1.33 g, 3.00 Eq, 6.08 mmol) is added and it was allowed to warm-up to rt overnight for 22 h. The reaction was quenched with brine (5 mL) at 0° C. and the methanol was removed under reduced pressure. Brine was added (500 mL) and the aqueous phase was extracted with diethyl ether (3×150 mL). The combined organic phases were washed with brine (100 mL), dried over sodium sulfate, filtered and concentrated to dryness to afford the crude material as yellowish oil (954 mg, 97%) which was used without further purification.

$^1$H NMR (400 MHz, DMSO) δ 6.69 (m, 4H), 2.96 (m, 8H), 1.57 (t, J=6.58 Hz, 4H), 1.42 (m, 34H). TLC-MS, $[M+H]^+$=485, [M+H−Boc]=385

(d) Bis-Amine-Hydrochloride-Precursor (v)

di-tert-butyl(((bicyclo[2.2.2]octane-1,4-diylbis(methylene))bis(oxy))bis(propane-3,1-diyl))dicarbamate (950 mg, 1.00 Eq, 1.96 mmol) was dissolved in HCl in dioxane (4-M) (4.90 mL, 10.0 Eq, 19.6 mmol) and stirred at rt for 14 h. The reaction mixture was concentrated under reduced pressure. The residue was triturated with diethyl ether (1×5 mL) and dried under reduced pressure. The crude product was afforded as yellowish solid (780 mg, quantitative yield).

$^1$H NMR (400 MHz, DMSO) δ 7.90 (s, 5H), 7.39-7.02 (m, 1H), 3.39 (t, J=6.0 Hz, 4H), 2.99 (s, 4H), 2.80 (m, 4H), 1.79-1.71 (m, 4H), 1.35 (s, 12H).

(e) Bis-Acid-Intermediate (vi)

A suspension of 3,3'-((bicyclo[2.2.2]octane-1,4-diylbis(methylene))bis(oxy))bis(propan-1-amine)dihydrochloride (730 mg, 1.00 Eq, 2.04 mmol) and TEA (584 μL, 2.05 Eq, 4.19 mmol) in chloroform (21 mL) is cooled to 0° C. Then maleic anhydride (401 mg, 2.00 Eq, 4.09 mmol) is added. The mixture is allowed to warm-up to rt for 22 h. Next morning water is added and the reaction mixture is acidified with 2-M HCl until pH=2. The aqueous phase is extracted with EtOAc (3×). The combined organic phases were dried over sodium sulfate, filtered and concentrated under reduced pressure. The crude material was afforded as colorless oil (755 mg, 77%) and used further without purification.

$^1$H NMR (400 MHz, DMSO) δ 9.13 (s, 2H), 6.37 (d, J=12.5 Hz, 2H), 6.23 (d, J=12.5 Hz, 2H), 3.21 (m, 4H), 2.97 (s, 4H), 1.69 (m, 4H), 1.34 (m, 16H). LC-MS (ESI+), $[M+H]^+$=481, $[M-H]^-$=479

(f) SPC-TB-0003

To a solution of (2Z,2'Z)-4,4'-((((bicyclo[2.2.2]octane-1,4-diylbis(methylene))bis(oxy))bis(propane-3,1-diyl))bis(azanediyl))bis(4-oxobut-2-enoic acid) (755 mg, 1.00 Eq, 1.57 mmol) in Acetone (10.5 mL) was added acetic anhydride (890 μL, 6.00 Eq, 9.43 mmol) and sodium acetate (103 mg, 0.80 Eq, 1.26 mmol). The mixture was refluxed for 16 h. After cooling to rt it was diluted with EtOAc and washed with sat. NaHCO3-solution. The organic phase was dried over sodium sulfate, filtered and concentrated to dryness. The crude material was purified by column chromatography (silica gel, EtOAc in Cyclohexane, gradient 0-60% EtOAc) to afford the title compound as colorless solid (62 mg, 9%).

$^1$H NMR (400 MHz, DMSO) δ 7.00 (s, 4H), 3.45 (t, J=6.9 Hz, 4H), 3.29 (t, J=6.0 Hz, 4H), 2.93 (s, 4H), 1.75-1.64 (m, 4H), 1.32 (s, 12H). TLC-MS, $[M+H]^+$=445

(g) Bis-Amino Intermediate (vii)

To a solution of of 3,3'-((bicyclo[2.2.2]octane-1,4-diylbis(methylene))bis(oxy))dipropanenitrile (7.59 g, 1.00 Eq, 27.5 mmol) in THF (245 mL) at 0° C. under nitrogen was slowly added 1M-$BH_3$*THF-complex solution in THF (137 mL, 5.00 Eq, 137 mmol) The reaction was stirred at 0° C. for 1 h and then refluxed for 1 h. After cooled to 0° C. again MeOH (78.7 mL) were added followed by conc. HCl (9.84 mL) and allowed to warm to rt for 1 h. Solvent was removed under reduced pressure (300 mbar, 40° C.) and the residue was basified with 2M NaOH and extracted with EtOAc (4×). Combined org. phases were washed with brine, dried over magnesium sulfate, filtered and concentrated under reduced pressure giving a colorless oil (8.3 g). The crude (not clean) was used without further purification.

(h) SPC-TB-0003

3,3'-((bicyclo[2.2.2]octane-1,4-diylbis(methylene))bis(oxy))bis(propan-1-amine) (500 mg, 1.00 Eq, 1.76 mmol) was suspended in sodium bicarbonate solution (13.5 mL). Mixture is cooled to 0° C. after which methyl 2,5-dioxo-2,5-dihydro-1H-pyrrole-1-carboxylate (545 mg, 2.00 Eq, 3.52 mmol) is added. Precipitation occurred which stopped stirring. 1,4-dioxane was added (5 mL) which did facilitate stirring. After 14 h (no stirring) at rt water was added and aq. phase was extracted with DCM (3×). Combined org. phases were washed with brine and concentrated under reduced pressure. The crude material was purified by column chromatography (silica gel, EtOAc in cyclohexane up to 100% EtOAc) giving the title compound as white solid (170 mg, 22%).

$^1$H NMR (400 MHz, DMSO) δ 7.00 (s, 4H), 3.45 (t, J=6.9 Hz, 4H), 3.29 (t, J=6.0 Hz, 4H), 2.93 (s, 4H), 1.75-1.64 (m, 4H), 1.32 (s, 12H). TLC-MS, $[M+H]^+$=445.

Example 5: Synthesis of Compound 5 (SPC-TB-0007)

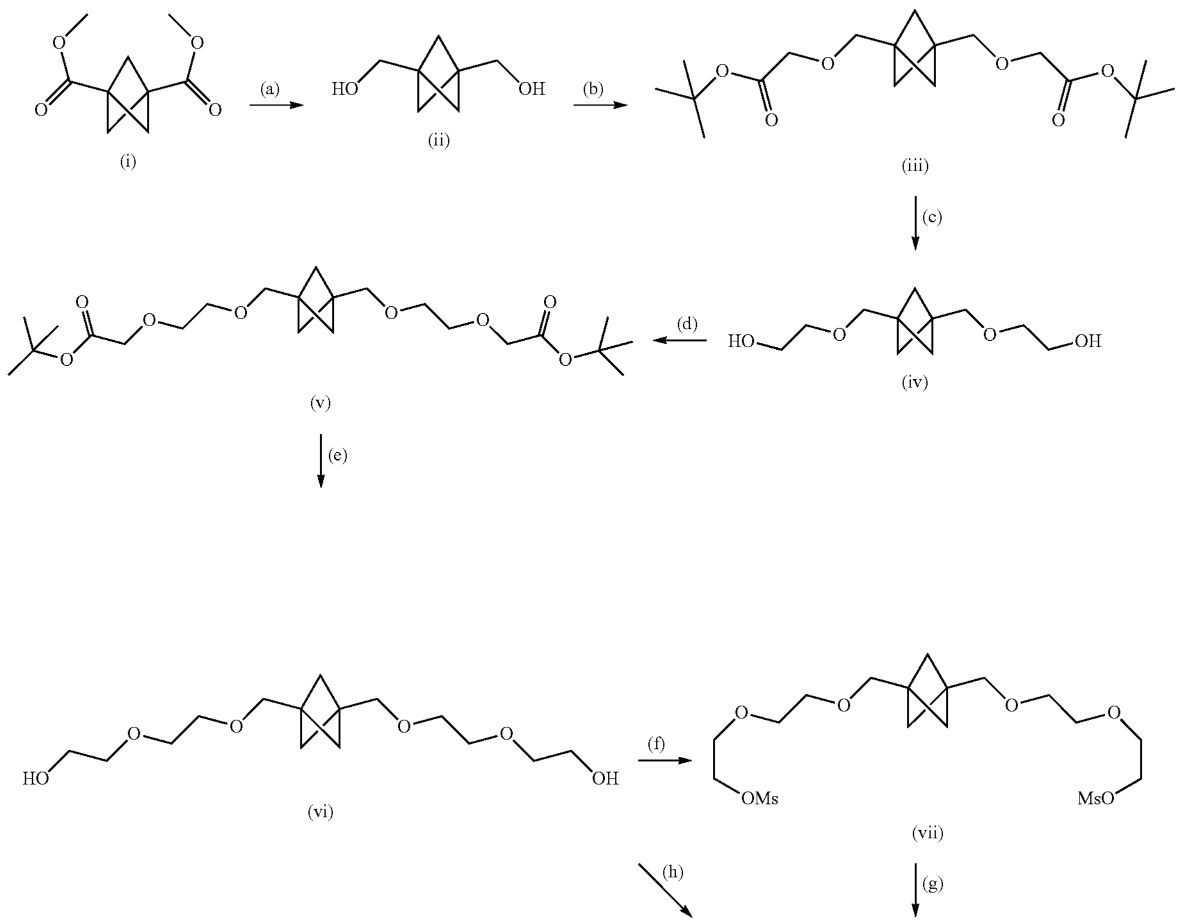

-continued

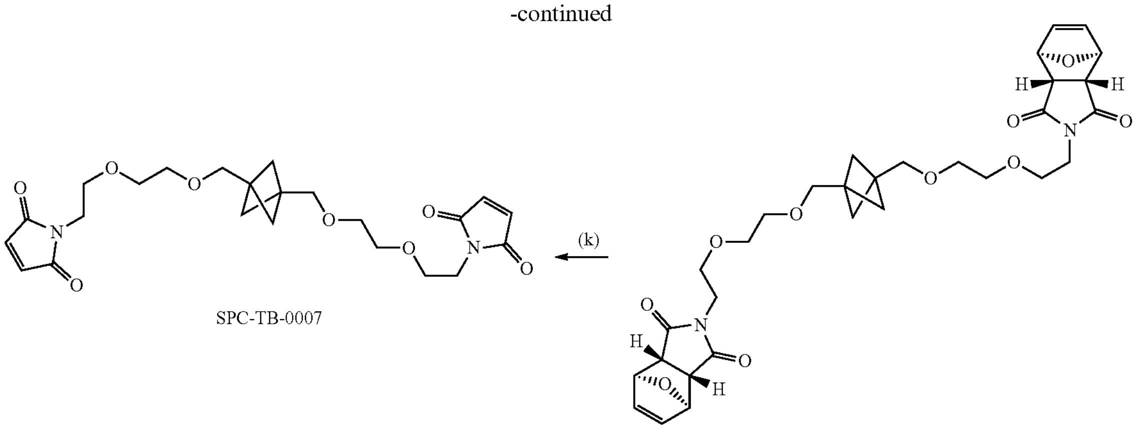

SPC-TB-0007

(viii)

(a) Diol (ii)

To a solution of dimethyl bicyclo[1.1.1]pentane-1,3-dicarboxylate (25.38 g, 1 eq., 137.8 mmol) at 0° C. in anhydrous THF (551 mL) under nitrogen was added dropwise a 2M solution of $LiAlH_4$ in THF (151.6 mL, 2.2 eq., 303.1 mmol). Temperature is maintained below 10° C. in the flask during the addition. The reaction mixture was stirred at rt. for 16 h. After reaction completion, Fieser work-up was performed to afford the desired product bicyclo[1.1.1]pentane-1,3-diyldimethanol (19.08 g, 148.9 mmol, quant.) as a transparent oil that solidified on standing.

The reaction was also performed on 50 g scale with mechanical stirring to produce 31.5 g of desired product (91% yield).

$^1$H NMR (400 MHz, DMSO) δ 4.39 (t, J=5.6 Hz, 2H), 3.35 (d, J=5.6 Hz, 4H), 1.45 (s, 6H).

(b) Diester (iii)

To a solution of bicyclo[1.1.1]pentane-1,3-diyldimethanol (500 mg, 1 eq., 3.90 mmol), tetrabutylammonium bromide (717 mg, 0.57 eq., 2.22 mmol) and tert-butyl 2-bromoacetate (6.09 g, 4.64 mL, 8 eq., 31.2 mmol) in toluene (12 mL) was added NaOH (33 w % aq solution, 24 mL). The reaction mixture was stirred vigorously at rt. for 16 h (yellow color develops). After reaction completion, the phases were separated and the toluene layer was collected. The aqueous layer was extracted with DCM (3×). Then, the combined organic layers were washed with brine, dried over anhydrous $MgSO_4$, and concentrated under vacuum. The residue was purified on silica (0% to 40% EtOAc in cyclohexane) to afford di-tert-butyl 2,2'-((bicyclo[1.1.1]pentane-1,3-diylbis(methylene))bis(oxy))diacetate (900 mg, 2.52 mmol, 64.7%) as a white solid.

$^1$H NMR (400 MHz, $CDCl_3$) δ 3.96 (s, 4H), 3.53 (s, 4H), 1.73 (s, 6H), 1.47 (s, 18H).

(c) Diol (iv)

To a solution of di-tert-butyl 2,2'-((bicyclo[1.1.1]pentane-1,3-diylbis(methylene))bis(oxy))diacetate (860 mg, 1 eq., 2.41 mmol) at 0° C. in anhydrous THF (12.1 mL) under nitrogen was added dropwise a 2M solution of $LiAlH_4$ in THF (201 mg, 2.65 mL, 2.00 molar, 2.2 eq., 5.31 mmol). The reaction mixture was stirred at rt. for 5 h. After reaction completion, Fieser work-up was performed to afford the desired product 2,2'-((bicyclo[1.1.1]pentane-1,3-diylbis(methylene))bis(oxy))bis(ethan-1-ol) (420 mg, 1.94 mmol, 80.5%) as a transparent oil.

$^1$H NMR (400 MHz, DMSO) δ 4.54 (t, J=5.4 Hz, 2H), 3.47 (tdd, J=6.1, 5.2, 1.1 Hz, 4H), 3.40-3.36 (m, 8H), 1.58 (s, 6H).

(d) Diester (v)

To a solution of 2,2'-((bicyclo[1.1.1]pentane-1,3-diylbis(methylene))bis(oxy))bis(ethan-1-ol) (3.40 g, 1 eq., 15.7 mmol), tetrabutylammonium bromide (2.89 g, 0.57 eq., 8.96 mmol) in toluene (48 mL) was added NaOH (33w % aq solution, 97 mL). The reaction mixture was stirred vigorously at rt for 16 h. After reaction completion (TLC), the phases were separated and the toluene layer was collected. The reaction mixture was stirred vigorously at rt. for 16 h (yellow color develops). After reaction completion, the phases were separated and the toluene layer was collected. The aqueous layer was extracted with DCM (3×). Then, the combined organic layers were washed with brine, dried over anhydrous $MgSO_4$, and concentrated under vacuum. The residue was chromatographed (0% to 40% EtOAc/cyclohexane) to afford the desired product di-tert-butyl 2,2'-((((bicyclo[1.1.1]pentane-1,3-diylbis(methylene))bis(oxy))bis(ethane-2,1-diyl))bis(oxy))diacetate (4.91 g, 11.0 mmol, 70.3%) as a transparent oil.

$^1$H NMR (400 MHz, $CDCl_3$) δ 4.03 (s, 4H), 3.73-3.61 (m, 8H), 3.48 (s, 4H), 1.68 (s, 6H), 1.48 (s, 18H).

(e) Diol (vi)

To a solution of di-tert-butyl 2,2'-((((bicyclo[1.1.1]pentane-1,3-diylbis(methylene))bis(oxy))bis(ethane-2,1-diyl))bis(oxy))diacetate (4.91 g, 1 eq., 11.0 mmol) at 0° C. in anhydrous THF (73.6 mL) under nitrogen was added dropwise a 1M solution of $LiAlH_4$ in THF (1.05 g, 27.6 mL, 1.00 molar, 2.5 Eq, 27.6 mmol). The reaction mixture was stirred at rt. for 5 h. After reaction completion, Fieser work-up was performed to afford the desired product 2,2'-((((bicyclo[1.1.1]pentane-1,3-diylbis(methylene))bis(oxy))bis(ethane-2,1-diyl))bis(oxy))bis(ethan-1-ol) (3.3 g, 11 mmol, 98%) as a transparent oil.

$^1$H NMR (400 MHz, DMSO) δ 4.55 (t, J=5.5 Hz, 2H), 3.54-3.35 (m, 20H), 1.58 (s, 6H).

(f) Di-mesylate (vii)

2,2'-((((bicyclo[1.1.1]pentane-1,3-diylbis(methylene))bis(oxy))bis(ethane-2,1-diyl))bis(oxy))bis(ethan-1-ol) (200 mg, 1 Eq, 657 μmol) was dissolved in DCM (3.29 mL) before TEA (332 mg, 458 μL, 5.00 Eq, 3.29 mmol) was added and the mixture was cooled to 0° C. Once cooled, methanesulfonyl chloride (301 mg, 203 μL, 4.00 Eq, 2.63 mmol) was added and the mixture was kept at 0° C. for 15 min before being allowed to warm to rt. After 2 h, the reaction was judged to be completed and was diluted with DCM and quenched with water. The layers were separated and the aqueous was extracted with DCM (3×). The combined organic layers were washed with brine, dried ($Na_2SO_4$), and concentrated under reduced pressure to provide ((((bicyclo[1.1.1]pentane-1,3-diylbis(methylene))bis(oxy))bis(ethane-2,1-diyl))bis(oxy))bis(ethane-2,1-diyl)dimethanesulfonate as a clear oil (yield assumed quantitative) which was taken into the next step directly without further purification.

$^1$H NMR (400 MHz, CDCl3) δ 4.42-4.34 (m, 4H), 3.80-3.75 (m, 4H), 3.68-3.57 (m, 8H), 3.45 (s, 4H), 3.07 (s, 6H), 1.66 (s, 6H).

(g) Substitution Product (viii)

((((bicyclo[1.1.1]pentane-1,3-diylbis(methylene))bis(oxy))bis(ethane-2,1-diyl))bis(oxy))bis(ethane-2,1-diyl)dimethanesulfonate (454 mg, 1 Eq, 0.986 mmol) was dissolved in MeCN (2 mL) before KI (32.7 mg, 0.2 Eq, 197 μmol), $K_2CO_3$ (545 mg, 4 Eq, 3.94 mmol), and 3a,4,7,7a-tetrahydro-1H-4,7-epoxyisoindole-1,3 (2H)-dione (Prepared according to Eur. J. Org. Chem, 2012, 31, 6165. without deviation from the protocol to produce only the exo isomer) (489 mg, 3 Eq, 2.96 mmol) were added. The mixture was heated to 70° C. for 18 h. The reaction showed 1:1 mixture of mono and di-substitution by LC-MS and an additional equivalent of 3a,4,7,7a-tetrahydro-1H-4,7-epoxyisoindole-1,3 (2H)-dione and $K_2CO_3$ were added. After 6 h, the reaction was cooled to rt and concentrated under reduced pressure. The residue was taken up in 1:1 mixture of EtOAc/$H_2O$ and the aqueous was extracted with EtOAc (5×). The organic layer was dried ($Na_2SO_4$), filtered, and concentrated under reduced pressure. The crude residue was purified on silica (80-100% EtOAc in Cyclohexane) to provide 2,2'-(((((bicyclo[1.1.1]pentane-1,3-diylbis(methylene))bis(oxy))bis(ethane-2,1-diyl))bis(oxy))bis(ethane-2,1-diyl))bis(3a,4,7,7a-tetrahydro-1H-4,7-epoxyisoindole-1,3 (2H)-dione) (248 mg, 414 μmol, 42.0%) and a colorless oil.

$^1$H NMR (400 MHz, DMSO) δ 6.55 (t, J=0.9 Hz, 4H), 5.12 (t, J=0.9 Hz, 4H), 3.52-3.42 (m, 16H), 3.35 (s, 4H), 2.93 (s, 4H), 1.56 (s, 6H).

(h) Substitution Product (viii)

Triphenylphosphine (194 mg, 2.25 Eq, 739 μmol) was dissolved in THF (2.05 mL) before being cooled to 0° C. DIAD (149 mg, 144 μL, 2.25 Eq, 739 μmol) was added slowly over 2-3 min. The yellow reaction mixture was stirred 5 min at 0° C. Then, 2,2'-((((bicyclo[1.1.1]pentane-1,3-diylbis(methylene))bis(oxy))bis(ethane-2,1-diyl))bis(oxy))bis(ethan-1-ol) (100 mg, 1 Eq, 329 μmol) was added as a solution in THF (2.05 mL) over 1 min and stirred for 5 min 0° C. Lastly, 3a,4,7,7a-tetrahydro-1H-4,7-epoxyisoindole-1,3 (2H)-dione (130 mg, 2.40 Eq, 788 μmol) was added to the reaction mixture as a solid. The resulting suspension was allowed to remain at 0° C. for 5 min during which time most of the maleimide dissolved. The cooling bath was then removed, and the reaction was stirred overnight at ambient temperature. The reaction was concentrated in vacuo and purified on silica (80 to 100% EtOAc in Cyclohexane, followed by 0 to 20% MeOH in DCM) to provide 2,2'-(((((bicyclo[1.1.1]pentane-1,3-diylbis(methylene))bis(oxy))bis(ethane-2,1-diyl))bis(oxy))bis(ethane-2,1-diyl))bis(3a,4,7,7a-tetrahydro-1H-4,7-epoxyisoindole-1,3 (2H)-dione) (0.12 g, 0.21 mmol, 63%, +4 w % $PPh_3O$) as an oil.

$^1$H NMR (400 MHz, DMSO) δ 6.55 (d, J=1.0 Hz, 4H), 5.12 (d, J=1.0 Hz, 4H), 3.55-3.41 (m, 16H), 3.35 (s, 4H), 2.93 (s, 4H), 1.56 (s, 6H).

(k) SPC-TB-0007

2,2'-(((((bicyclo[1.1.1]pentane-1,3-diylbis(methylene))bis(oxy))bis(ethane-2,1-diyl))bis(oxy))bis(ethane-2,1-diyl))bis(3a,4,7,7a-tetrahydro-1H-4,7-epoxyisoindole-1,3 (2H)-dione) (248 mg, 1 Eq, 414 μmol) was dissolved in toluene (18 mL) and heated to reflux overnight (Bath temperature set at 120° C., reflux condenser open to air). TLC indicated full consumption of the SM and the reaction was concentrated under reduced pressure. The crude was purified on silica (50-80% EtOAc in Cyclohexanes) to produce 1,1'-(((((bicyclo[1.1.1]pentane-1,3-diylbis(methylene))bis(oxy))bis(ethane-2,1-diyl))bis(oxy))bis(ethane-2,1-diyl))bis(1H-pyrrole-2,5-dione) (89 mg, 0.19 mmol, 46%) as a colorless oil which solidified on standing.

$^1$H NMR (400 MHz, DMSO) δ 7.02 (s, 4H), 3.60-3.40 (m, 16H), 3.33 (s, 4H), 1.53 (s, 6H). TLC-MS (APCI): $[M+H]^+$=463.4.

(k) SPC-TB-0007 from vi)

$PPh_3$ (2.90 g, 2.25 Eq, 11.09 mmol) was dissolved in THF (30.8 mL) before being cooled to 0° C. DIAD (2.24 g, 2.16 mL, 2.25 Eq, 11.09 mmol) was added slowly over 5 min. The yellow reaction mixture was stirred 10 min at 0° C. Then, 2,2'-((((bicyclo[1.1.1]pentane-1,3-diylbis(methylene))bis(oxy))bis(ethane-2,1-diyl))bis(oxy))bis(ethan-1-ol) (1.50 g, 1 Eq, 4.93 mmol) was added dropwise as a solution in THF (30.8 mL) and stirred for an additional 5 min at 0° C. After this time, protected maleimide (endo/exo mix) (1.95 g, 2.40 Eq, 11.83 mmol) was added to the reaction mixture as a solid. The resulting suspension was allowed to remain at 0° C. for 5 min during which time most of the maleimide dissolved. The cooling bath was then removed, and the reaction was stirred overnight at ambient temperature. The reaction was concentrated under reduced pressure and the crude residue dissolved in ethanol (14.93 mL) and warmed to 30° C. to obtain a clear solution. A 30° C. solution of $ZnCl_2$ (2.85 g, 2 Eq, 20.9 mmol) in EtOH (14.93 mL) was added while under vigorous stirring and was left overnight at rt (while stirring) and a white precipitate formed. The precipitate was filtered and rinsed with EtOH. After concentration under reduced pressure the crude brown oil was purified on silica (80 to 100% EtOAc in Cyclohexane) to provide a mixture of endo-endo, endo-exo, and exo-exo and deprotected product (2.64 g, precise distribution of products not determined).

The yellow oil was dissolved in toluene (193 mL) and heated to reflux overnight (bath temperature set at 120° C., reflux condenser open to air). The reaction was concentrated under reduced pressure and the crude was purified on silica (50-80% EtOAc in Cyclohexanes) to produce 1,1'-(((((bicyclo[1.1.1]pentane-1,3-diylbis(methylene))bis(oxy))bis(ethane-2,1-diyl))bis(oxy))bis(ethane-2,1-diyl))bis(1H-pyrrole-2,5-dione) (1.086 g, 2.348 mmol, 47.65%) as a clear oil which solidifies on standing.

Example 6: Synthesis of Compound 6 (SPC-TB-0013)

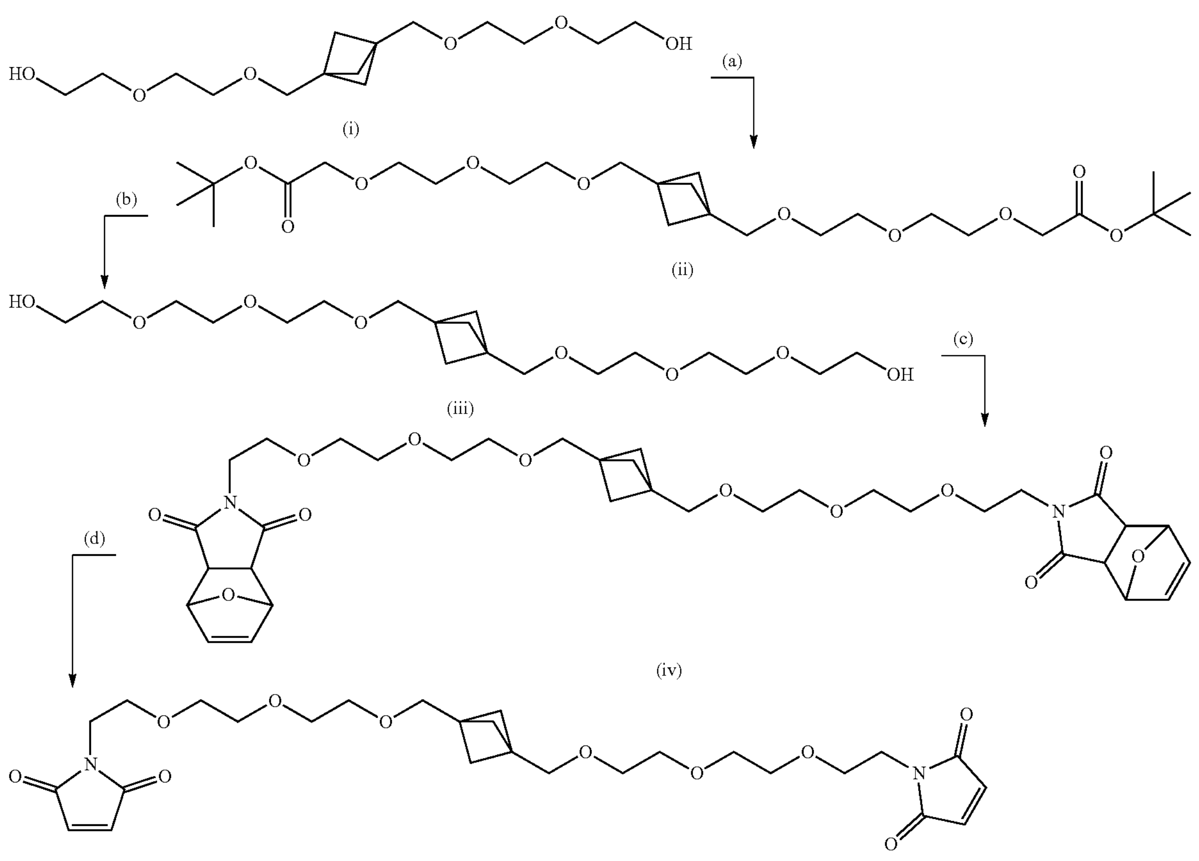

SPC-TB-0013

(a) Diester (ii)

To a solution of 2,2'-((((bicyclo[1.1.1]pentane-1,3-diylbis(methylene))bis(oxy))bis(ethane-2,1-diyl))bis(oxy))bis(ethan-1-ol) (3.0 g, 1.0 eq., 9.9 mmol), tetrabutylammonium bromide (1.80 g, 0.57 eq., 5.60 mmol) and tert-butyl 2-bromoacetate (15.0 g, 12.0 mL, 8 eq., 79.0 mmol) in toluene (30 mL) was added NaOH (33w % aq solution, 61 mL). The reaction mixture was stirred vigorously at rt for 16 h. After reaction completion (TLC), the phases were separated and the toluene layer was collected. The aq. layer was extracted with DCM (3×). Then, the combined organic layers were washed with brine, dried over anhydrous $MgSO_4$, and concentrated under vacuum. The residue was chromatographed (30% to 60% EtOAc/cyclohexane) to afford the desired product di-tert-butyl 2,2'-((((((bicyclo[1.1.1]pentane-1,3-diylbis(methylene))bis(oxy))bis(ethane-2,1-diyl))bis(oxy))bis(ethane-2,1-diyl))bis(oxy))diacetate (2.35 g, 4.41 mmol, 45.0%) as a yellowish oil.

1H NMR (400 MHz, $CDCl_3$) 4.02 (s, 4H), 3.70 (m, 8H), 3.62 (m, 8H), 3.47 (s, 4H), 1.67 (s, 6H), 1.47 (s, 18H). TLC-MS (APCI): $[M+H]^+$=420.7 (minus the two t-Bu groups).

(b) Diol (iii)

To a solution of di-tert-butyl 2,2'-((((((bicyclo[1.1.1]pentane-1,3-diylbis(methylene))bis(oxy))bis(ethane-2,1-diyl))bis(oxy))bis(ethane-2,1-diyl))bis(oxy))diacetate (2.15 g, 1 eq., 4.04 mmol) at 0° C. in anhydrous THF (40.4 mL) under nitrogen was added dropwise a solution of $LiAlH_4$ in THF (4.44 mL, 2.00 molar, 2.2 Eq, 8.88 mmol). The reaction mixture was allowed to warm-up for 17 h o/n. After reaction completion, Fieser work-up was performed to afford the desired product 2,2'-((((((bicyclo[1.1.1]pentane-1,3-diylbis(methylene))bis(oxy))bis(ethane-2,1-diyl))bis(oxy))bis(ethane-2,1-diyl))bis(oxy))bis(ethan-1-ol) (1.46 g, 4.04 mmol, 92%) as a transparent oil.

$^1H$ NMR (400 MHz, $CDCl_3$) 3.73 (m, 4H), 3.64 (m, 20H), 3.47 (s, 4H), 1.68 (s, 6H).

(c) Substitution Product (iv)

A microwave vial tube was charged with triphenylphosphine (150 mg, 2.25 Eq, 573 μmol) to which was added THF (1.59 mL). The resulting clear solution was cooled to 0° C. DIAD (116 mg, 111 μL, 2.25 Eq, 573 μmol) was added slowly over 2-3 min. The yellow reaction mixture was stirred 5 min at 0° C. Then 2,2'-((((((bicyclo[1.1.1]pentane-1,3-diylbis(methylene))bis(oxy))bis(ethane-2,1-diyl))bis(oxy))bis(ethane-2,1-diyl))bis(oxy))bis(ethan-1-ol) (100 mg, 1 Eq, 255 μmol) was added over 1 min and stirred for 5 min. At last 3a,4,7,7a-tetrahydro-1H-4,7-epoxyisoindole-1,3 (2H)-dione (101 mg, 2.40 Eq, 611 μmol) was added to the reaction mixture as a solid. The resulting suspension was allowed to remain at 0° C. for 5 min during which time most of the maleimide dissolved. The cooling bath was then removed, and the reaction was stirred overnight (18 h) at ambient temperature. Afterwards the reaction mixture was concentrated in vacuo and passed through silica eluting with 15% MeOH in DCM to produce the title compound with some impurities by TLC which was taken into the next step without further purification.

TLC-MS (APCI): $[M+H]^+$=551.1 (minus furan protecting groups).

(d) SPC-TB-0013

2,2'-(((((((bicyclo[1.1.1]pentane-1,3-diylbis(methylene)) bis(oxy))bis(ethane-2,1-diyl))bis(oxy))bis(ethane-2,1-diyl)) bis(oxy))bis(ethane-2,1-diyl))bis(3a,4,7,7a-tetrahydro-1H-4,7-epoxyisoindole-1,3(2H)-dione) (175 mg, 1.0 eq., 255 μmol) was suspended in toluene (11.1 mL) and refluxed overnight for 18 h. Upon full consumption of starting material the reaction mixture was concentrated and the residue purified by column chromatography (silica gel, EtOAc in Cyclohexane 60-80%) to afford the title compound as colorless oil (87 mg, 62%, yield over two steps).

$^1$H NMR (400 MHz, DMSO): 7.02 (s, 4H), 3.46 (m, 24H), 3.32 (s, 4H), 1.57 (s, 6H). TLC-MS (APCI): $[M+H]^+$=551.1

Example 7: Synthesis of Compound 7 (SPC-TB-0014)

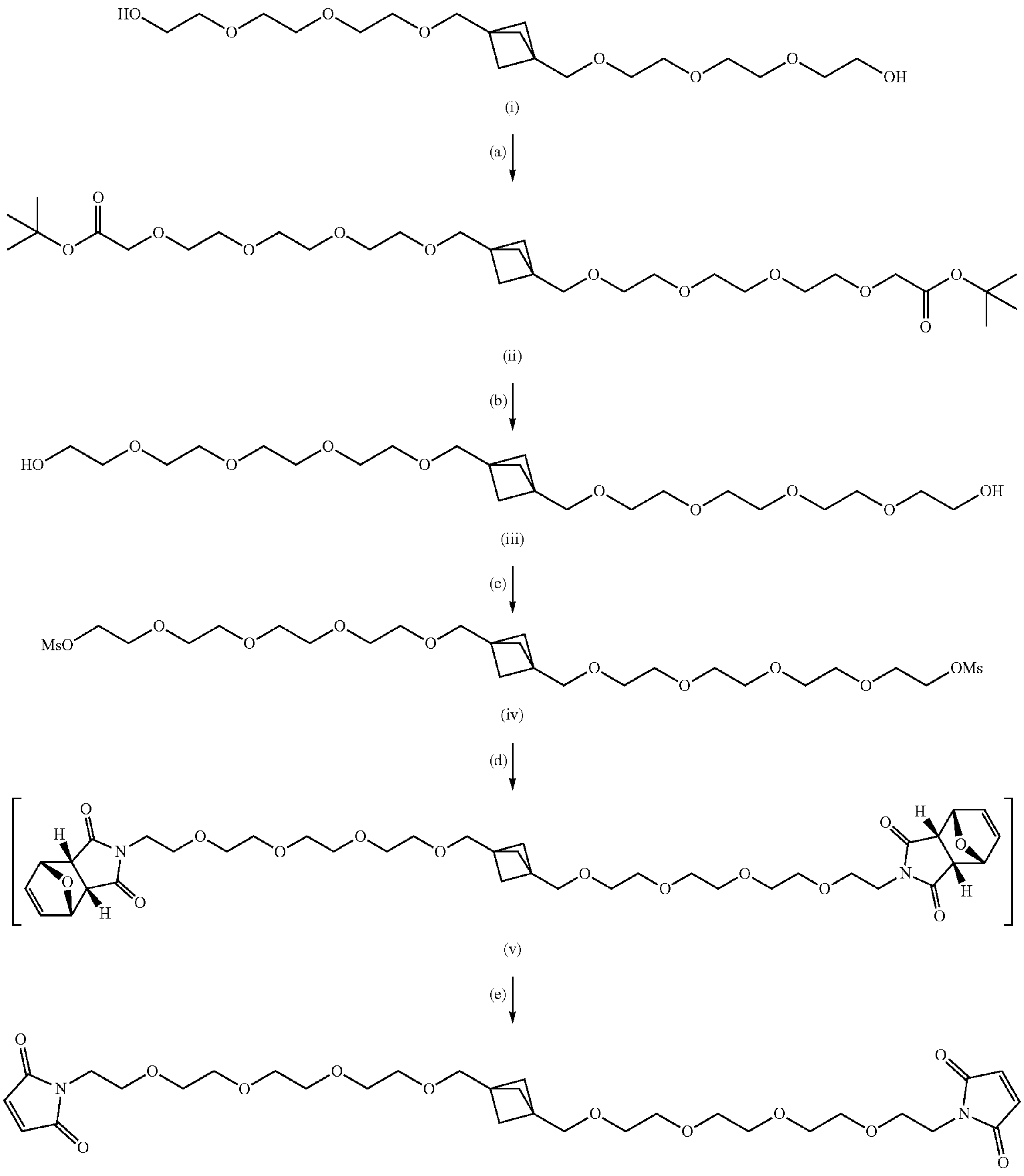

SPC-TB-0014

(a) Diester (ii)

To a solution of 2,2'-((((((bicyclo[1.1.1]pentane-1,3-diylbis(methylene))bis(oxy))bis(ethane-2,1-diyl))bis(oxy))bis(ethane-2,1-diyl))bis(oxy))bis(ethan-1-ol) (1.46 g, 1.0 eq., 3.72 mmol), tetrabutylammonium bromide (0.68 g, 0.57 eq., 2.12 mmol) and tert-butyl 2-bromoacetate (5.80 g, 4.43 mL, 8 eq., 29.8 mmol) in toluene (11.4 mL) was added NaOH (33w % aq. solution, 22.9 mL) at 0° C. The reaction mixture was allowed to warm to rt for 17 h. After completion (TLC), the phases were separated and the toluene layer was collected. The aq. layer was extracted with DCM (3×, difficult separation, takes time). The combined organic layers were washed with brine, dried over magnesium sulfate, filtered and concentrated under vacuum. The residue was purified by column chromatography (10% to 60% EtOAc/cyclohexane) to afford the title compound di-tert-butyl 1,1'-(bicyclo[1.1.1]pentane-1,3-diyl)bis(2,5,8,11-tetraoxatridecan-13-oate) as yellow oil (1.31 g, 56.7%).

$^1$H NMR (400 MHz, $CDCl_3$): 4.01 (s, 4H), 3.71 (m, 8H), 3.66 (m, 8H), 3.62 (m, 8H), 3.47 (s, 4H), 1.67 (s, 4H), 1.47 (s, 18H). TLC-MS (APCI): 508 (minus 2× t-butyl ester)

(b) Diol (iii)

To a solution of di-tert-butyl 1,1'-(bicyclo[1.1.1]pentane-1,3-diyl)bis(2,5,8,11-tetraoxatridecan-13-oate) (1.31 g, 1 Eq, 2.11 mmol) in anhydrous THF (152 mg, 21.1 mL, 0.100 molar, 1 Eq, 2.11 mmol) at 0° C. under nitrogen was added dropwise a 2M-solution of LAH (176 mg, 2.32 mL, 2.2 Eq, 4.64 mmol) in THF. Temp. was kept below 10° C.

The resulting suspension was allowed to warm-up to rt. Next morning reaction mixture was not stirring anymore (diluted by half to get it stirring). TLC shows full conversion of sm after 18 h. Upon completion of reaction a Fieser work-up was performed. The title compound was isolated as colorless oil (1.03 g, quant. yield).

$^1$H NMR (400 MHz, $CDCl_3$): 3.66 (m, 32H), 3.46 (s, 4H), 1.67 (s, 6H). TLC-MS (APCI): $[M+H]^+$=481.1.

(c) Di-mesylate (iv)

A mixture of 1,1'-(bicyclo[1.1.1]pentane-1,3-diyl)bis(2,5,8,11-tetraoxatridecan-13-ol) (100 mg, 1.00 Eq, 0.21 mmol) and triethyl amine (116 µL, 4.00 Eq, 0.83 mmol) in DCM (1.04 mL) was cooled to 0° C. Methanesulfonyl chloride (48.3 µL, 3.00 Eq, 0.62 mmol) was added. The reaction mixture was stirred for 15 min at 0° C. and was allowed to warm-up to rt for 2 h. Upon completion of the reaction it was diluted with DCM, water was added, the phases were separated and the aqueous phase was extracted with DCM (3×). The combined organic phases were washed with brine, dried over magnesium sulfate, filtered and concentrated to dryness under reduced pressure. 146 mg (110%) of crude material was isolated which was used further without purification.

$^1$H NMR (400 MHz, CDCl3) δ 3.67-3.60 (m, 32H), 3.47 (s, 4H), 3.08 (s, 6H), 1.67 (s, 6H).

(d) Substitution Product (v)

Bicyclo[1.1.1]pentane-1,3-diylbis(2,5,8,11-tetraoxatridecane-1,13-diyl)dimethanesulfonate (146 mg, 229 µmol, 1.00 Eq.) was dissolved in MeCN (4.50 mL). KI (7.61 mg, 45.9 µmol, 0.20 Eq.), $K_2CO_3$ (158 mg, 1.15 mmol, 5.00 Eq.) and (3aR,4R,7S,7aS)-3a,4,7,7a-tetrahydro-1H-4,7-epoxyisoindole-1,3(2H)-dione (114 mg, 688 µmol, 3.00 Eq) were added. The mixture was heated to 70° C. for 44 h. After cooling to rt it was concentrated, taken up again in DCM, filtered (wash with ether) and concentrated. TLC-MS (APCI): $[M+H]^+$=774 (furan-protected intermediate).

(e) SPC-TB-0014

The concentrated material from the previous step was suspended in toluene (5.00 mL) and heated to reflux for 5 h. TLC shows partial conversion into product. The reaction mixture was concentrated and filtered through silica gel eluting with DCM/MeOH 0-10% MeOH. The filtrate was concentrated in vacuo and TLC-MS confirms the presence of product. The mixture was not purified further.

TLC-MS (APCI): $[M+H]^+$=639

Example 8: Thiol Recombination

General Procedure

The compound to be tested (1 eq.) was dissolved in an aqueous media (0.02-0.05 M) and 4 eq. of cysteine reagent (N-Fmoc-cysteine (C1) or N-Cbz-cysteine (C2)) were added. Two test solutions were used as aqueous media: test solution 1 was a phosphate buffer (pH=5.4) with or without an emulsifier (e.g. Eumulgin) and test solution 2 was an aqueous solution containing 0.49% (w/w) sodium benzoate and 0.30% (w/w) citric acid with or without an emulsifier (e.g. Eumulgin).

To make the phosphate buffer a solution of 0.1-M solution of citric acid (use citric acid monohydrate) and a 0.2-M solution of $Na_2HPO_4$ (use $Na_2HPO_4$ or $Na_2HPO_4*2H_2O$) were prepared and mixed with the following ratio: 44.25 mL/55.75 mL=mL 0.1M-citric acid/mL 0.2M $Na_2HPO_4$ to give a buffer solution with pH=5.4.

The tests were performed at ambient temperature of 30° C. under stirring with small magnetic stirrers in LC-MS vials or small glass vials (see picture 1). The reactions were performed under normal atmosphere. The reactions were monitored by LC-MS. The reaction scale was between 4 and 10 mg of tested compound. To calculate the conversion into products the ratio between cysteine reagent, mono-Michael-addition product (mono) and bis-Michael-addition product (bis) as shown in the following schemes were compared.

All compounds show comparable or improved reactivity with the cysteine derivative compared to the reference compounds.

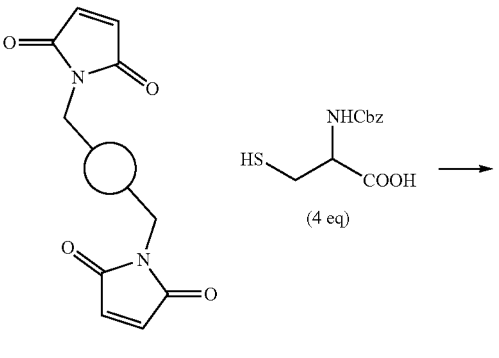

-continued

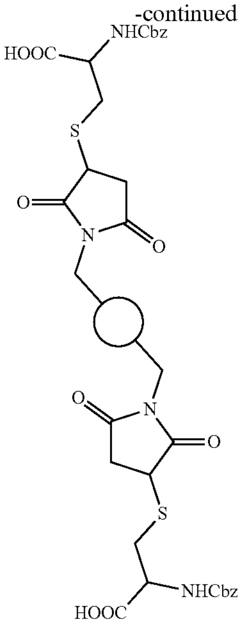

bis

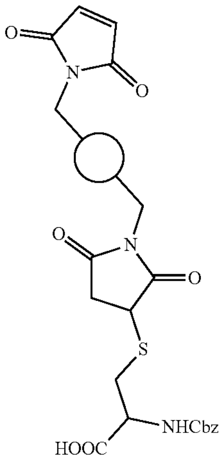

mono

Results (reaction conditions: test solution 1 (pH=5.4); 0.05M, 30° C.)

| Test compound | Conversion at 15 min | Conversion at 30 min | Conversion at 60 min |
|---|---|---|---|
| Reference compound #1 | 9% bis<br>0% mono | 10% bis<br>0% mono | 22% bis<br>29% mono |
| SPC-TB-0002 | 17% bis<br>0% mono | 11% bis<br>0% mono | 10% bis<br>0% mono |
| SPC-TB-0001 | 15% bis<br>0% mono | 28% bis<br>0% mono | 21% bis<br>0% mono |
| SPC-TB-0003 | 29% bis<br>9% mono | 77% bis<br>10% mono | — |
| SPC-TB-0007 | 24% bis<br>47% mono | 22% bis<br>66% mono | 50% bis<br>37% mono |

Results (reaction conditions: test solution 2+1% Eumulgin; 0.02M, 30° C.)

| Tested compound | Conversion at 30 min | Conversion at 60 min |
|---|---|---|
| Reference compound #1 | 30% bis<br>30% mono | 56% bis<br>9% mono |
| SPC-TB-0007 | 26% bis<br>26% mono | 44% bis<br>10% mono |
| SPC-TB-0013 | 36% bis<br>10% mono | 50% mono and bis* |

*peaks are not separated in LC-MS

Results (reaction conditions: test solution 1 (pH=5.4)+1% eumulgin; 0.02M, 30° C.)

| Tested compound | Conversion at 30 min | Conversion at 60 min |
|---|---|---|
| Reference compound #1 | 50% bis<br>0% mono | 60% bis<br>0% mono |
| SPC-TB-0007 | 53% bis<br>20% mono | 67% bis<br>9% mono |
| SPC-TB-0013 | 67% bis<br>16% mono | 66% bis<br>15% mono |

Results (reaction conditions: test solution 1 (pH=5.4)+2.5% eumulgin; 0.02M, 30° C.)

| Tested substrate | Conversion at 30 min | Conversion at 60 min | Conversion at 5 h |
|---|---|---|---|
| Reference compound #1 | 97% bis | 88% bis | 82% bis |
| Olaplex active agent = reference compound #2 | 4% bis | 7% bis | 18% bis |
| SPC-TB-0007 | 79% bis | 79% bis | 73% bis |
| SPC-TB-0013 | 57% bis | 57% bis | 46% bis |

The invention claimed is:

1. A compound of formula II or a pharmaceutically acceptable salt thereof

II

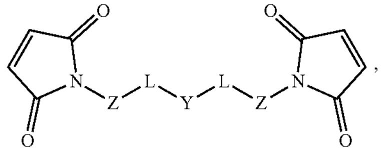

wherein:

Y is a $C_{3-11}$ bicycloalkyl,

L is $CH_2$, and

Z is straight-chain or branched $C_{1-13}$ alkyl, wherein one or more $CH_2$ groups are independently replaced by $—(CH_2—O—CH_2)—$, $—(CH_2—CH_2—O)—$, $—(O—CH_2—CH_2)—$, —O—, —NH— or —NR—, wherein R is linear or branched $C_{1-6}$ alkyl.

2. A compound according to claim 1 or a pharmaceutically acceptable salt thereof, wherein Y is a $C_{4-11}$ bridged bicycloalkyl.

3. A compound according to claim 1 or a pharmaceutically acceptable salt thereof, having formula III

III

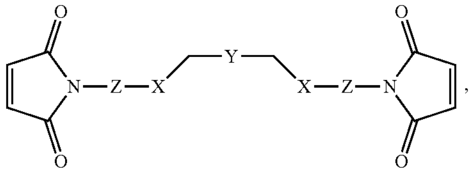

wherein:

Y is a $C_{4-11}$ bicycloalkyl,

X is selected from O, NH and NR, wherein R is linear or branched $C_{1-6}$ alkyl, and Z is straight-chain or branched $C_{1-12}$ alkyl, wherein one or more $CH_2$ groups may independently be replaced by $—(CH_2—O—CH_2)—$, $—(CH_2—CH_2—O)—$, $—(O—CH_2—CH_2)—$, —O—, —NH—, and —NR—, wherein R is branched or linear $C_{1-6}$ alkyl.

4. A compound according to claim 1 having formula IV or a pharmaceutically acceptable salt thereof

IV

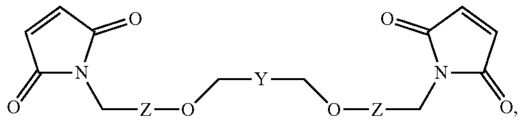

wherein:

Y is a $C_{5-11}$ bridged bicycloalkyl, and

Z is straight-chain or branched $C_{1-11}$ alkyl, wherein one or more $CH_2$ groups may independently be replaced by $—(CH_2—O—CH_2)—$, $—(CH_2—CH_2—O)—$, $—(O—CH_2—CH_2)—$, —O—, —NH—, and —NR—, wherein R is branched or linear $C_{1-6}$ alkyl.

5. A compound according to claim 1 having formula V or a pharmaceutically acceptable salt thereof

V

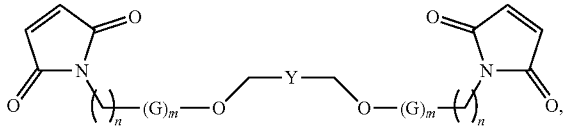

wherein:

Y is a $C_{5-11}$ bridged bicycloalkyl,

G is $—(CH_2—O—CH_2)—$, $—(CH_2—CH_2—O)—$, $—(O—CH_2—CH_2)—$, n is 1 to 4, and m is 0 to 8.

6. A compound according to claim 5 or a pharmaceutically acceptable salt thereof wherein either Y is bicyclo[1.1.1]pentane, n is 2 or 3, and m is 0, 1, 2 or 3;

or Y is bicyclo[2.2.2]octane, n is 3, and m is 0.

7. A compound according to claim 1 or a pharmaceutically acceptable salt thereof, wherein Y is selected from bicyclo[1.1.1]pentane, bicyclo[2.1.1]hexane, bicyclo[2.2.1]heptane, bicyclo[3.1.1]heptane, bicyclo[2.2.2]octane, and bicyclo[3.2.1]octane.

8. Cosmetic preparations comprising at least one compound according to claim 1 or a pharmaceutically acceptable salt thereof.

9. Cosmetic preparations according to claim 8 further comprising at least one cosmetic additive selected from the group consisting of surfactants, oil components, emulsifiers, pearlescent waxes, consistency-enhancing agents, thickeners, superfatting agents, stabilizers, polymers, silicone compounds, fats, waxes, lecithins, phospholipids, UV light protection factors, humectants, biogenic agents, antioxidants, deodorants, antiperspirants, antidandruff agents, film-forming agents, swelling agents, insect repellents, self-tanning agents, tyrosine inhibitors (depigmentation agents), hydrotropes, solubilizers, preservatives, perfumed oils and dyes, and mixtures thereof.

10. Cosmetic preparations according to claim 8 further comprising a carrier.

11. A method for treatment of keratin materials, the method comprising applying to the keratin materials a compound according to claim 1.

12. The method according to claim 11 wherein the keratin materials are comprised in hair.

13. A compound according to claim 5 wherein n is 2 or 3, and m is 0 to 3.

14. Cosmetic preparations according to claim 10 wherein the carrier is selected from water, C(2-6)-alcohols, C(1-10) polyols, and oil components.

* * * * *